(12) United States Patent
Concibido et al.

(10) Patent No.: US 8,987,547 B1
(45) Date of Patent: Mar. 24, 2015

(54) METHODS FOR CHARACTERIZING SOYBEAN APHID BIOTYPES

(75) Inventors: Vergel Concibido, Maryland Heights, MO (US); David Hoffman, Sioux Falls, SD (US); James Narvel, Middletown, DE (US); Jennifer Yates, Elkton, MD (US)

(73) Assignee: Monsanto Technology LLC, St. Louis, MO (US)

( * ) Notice: Subject to any disclaimer, the term of this patent is extended or adjusted under 35 U.S.C. 154(b) by 918 days.

(21) Appl. No.: 12/473,836

(22) Filed: May 28, 2009

Related U.S. Application Data

(60) Provisional application No. 61/056,667, filed on May 28, 2008.

(51) Int. Cl.
*A01H 1/04* (2006.01)
*C12Q 1/68* (2006.01)

(52) U.S. Cl.
USPC .......................... 800/267; 800/265; 800/312

(58) Field of Classification Search
None
See application file for complete search history.

(56) References Cited

U.S. PATENT DOCUMENTS

| | | | |
|---|---|---|---|
| 2005/0249769 | A1 | 11/2005 | Zhu et al. |
| 2006/0015964 | A1 * | 1/2006 | Hill et al. ................... 800/279 |
| 2006/0277627 | A1 | 12/2006 | Wang et al. |
| 2006/0288444 | A1 | 12/2006 | McCarroll et al. |
| 2007/0039065 | A1 | 2/2007 | Laurie |
| 2008/0226753 | A1 * | 9/2008 | Cosgrove ................... 424/725 |
| 2009/0049565 | A1 | 2/2009 | Concibido et al. |
| 2009/0241214 | A1 | 9/2009 | Wang et al. |
| 2010/0024073 | A1 | 1/2010 | Wang et al. |
| 2012/0174246 | A1 | 7/2012 | Chaky et al. |

FOREIGN PATENT DOCUMENTS

WO     2006/125065 A2     11/2006

OTHER PUBLICATIONS

Mensah et al. Crop Sci. 45: 2228-2233, 2005.*
Kim et al. ASA-CSSA-SSSA 2007 International Annual Meetings, Tuesday, Nov. 6, 2007, p. 159-3.*
Hesler et al. Euphytica 154: 91-99, 2007 (published online Oct. 17, 2006).*
Allard, R.W. p. 367 In: Principles of Plant Breeding, John Wiley & Sons: New York (1964).*
Curtis B. Hill et al., Resistance to the Soybean Aphid in Soybean Germpiasm, Crop Science Society of America, 44:98-106 (2004), Madison, WI.
Soybean Aphid Research Update, pp. 1-12. North Central Soybean; Research Program (2008).
Article entitled Aphid-resistant soybeans are a new option by Top Crop Manager, pp. 1-4, May 19, 2009 from http://www.topcropmanager.com/content/view/4424/67/.
Sinclair and Backman, Compendium of Soybean Disease, 3rd Ed. APS Press, St. Paul, MN, p. 1 (1989).
Cox of al., Relationship Between Coefficient of Parentage and Genetic Similarity Induces in the Soybean Crop Sci. 25:529-532 (1985).
Vennette et al., Assessing the Invasion by Soybean Aphid (Homoptera: Aphididae): Where Will It End?, Annals of the Entornological Society of America, 97(2):219-226 (Mar. 2004).
Wang et al., Plant Protection 4, 20:12-13 (1994).
Landis et al., NCR-125 Arthropod Biological Control: State Reports for 2003. http://www.ncera125.ent.msu.edu/StateRpts2003MI.htm.
Li et al., Soybean aphid resistance genes in the soybean cultivars Dowling and Jackson map to linkage group M. Mol Breeding, 19:25-34 (2007).
Gomez et al., Diurnal pattern of aphid feeding and its effect on cotton leaf physiology, Environmental and Experimental Botany, 55:77-86 (2006).
Wang et al., Aphis glycines as a Vector of Persistently and Nonpersistently Transmitted Viruses and Potential Risks for Soybean and Other Crops, Plant Disease 90:920-926 (Jul. 2006).
Kim et al., Discovery of Soybean Aphid Biotypes, Crop. Sci. 48:923-928 (2008).
Hill, CB; Li, Y; Hartman, GL; Soybean aphid resistance in soybean Jackson is controlled by a single dominant gene, Crop Science, 46 (4): 1606-1608 Jul.-Aug. 2006.
Hill, CB; Li, Y; Hartman, GL; A Single dominant gene for resistance to the soybean aphid in the soybean cultivar Dowling, Crop Science, 46 (4): 1601-1605 Jul.-Aug. 2006.
Narvel et al. A retrospective DNA marker assessment of the development of insect resistant soybean. Crop Science 41:1931-1939. 2001.
Venette et al. Assessing the Invasion by Soybean Aphid (Homoptera: Aphididae): Where Will It End?. Annals of the Entomological Society of America 97: 219-226. 2004.
Ha et al., Development of SNP Assays for Marker-Assisted Selection of Two Southern Root-Knot Nematode Resistance QTL in Soybean, Crop Science 47:S73-S82 (2007).
Mensah, Inheritance of Soybean Aphid Resistance in PI 567541B an dP1567598B, ASA-CSSA-SSSA, 2006 International Meetings.
Mensah, Identification of QTLs Underlying Soybean Aphid Resistance in PI 567598B, ASA-CSSA-SSSA, 2006 International Meetings.
Rafalski, Applications of single nucleotide polymorphisms in crop genetics, Current Opinion in Plant Biology, 5:94-100 (2002).

* cited by examiner

*Primary Examiner* — David T Fox
(74) *Attorney, Agent, or Firm* — Thompson Coburn LLP; William A. Holtz

(57) ABSTRACT

The present invention is directed, in various embodiments, to methods for characterizing soybean aphid biotypes, evaluating soybean plants for soybean aphid biotype resistance, producing a soybean plant having at least partial resistance to a soybean aphid biotype, and maintaining the biodiversity of soybean aphid biotypes from particular locations under laboratory conditions.

21 Claims, No Drawings

US 8,987,547 B1

METHODS FOR CHARACTERIZING SOYBEAN APHID BIOTYPES

CROSS-REFERENCE TO RELATED APPLICATIONS

This application claims the benefit under 35 U.S.C. §119 (e) of U.S. Provisional Application No. 61/056,667 filed May 28, 2008, the entirety of which is hereby incorporated by reference.

INCORPORATION OF THE SEQUENCE LISTING

A sequence listing containing the file named "pa_53776D.txt" which is 48,132 bytes (measured in Microsoft Windows®) and created on May 4, 2009, comprises 115 nucleotide sequences, and is herein incorporated by reference in its entirety.

FIELD OF THE INVENTION

The present invention relates to the field of soybean aphid biotypes and soybean aphid resistant plants.

BACKGROUND OF THE INVENTION

Soybean, *Glycine max* (L.) Merril, is a major economic crop worldwide and is a primary source of vegetable oil and protein (Sinclair and Backman, *Compendium of Soybean Diseases*, 3rd Ed. APS Press, St. Paul, Minn., p. 106. (1989). The growing demand for low cholesterol and high fiber diets has also increased the importance of the soybean as a health food.

Soybean varieties grown in the United States have a narrow genetic base, originating from Chinese strains. Six introductions, 'Mandarin,' 'Manchu,' 'Mandarin' (Ottawa), "Richland,' 'AK' (Harrow), and 'Mukden,' contributed nearly 70% of the germplasm represented in 136 cultivar releases. To date, modern-day cultivars can be traced back from these six Chinese soybean strains. In a study conducted by Cox et al., *Crop Sci.* 25:529-532 (1988), the soybean germplasm is comprised of 90% adapted materials, 9% unadapted, and only 1% exotic species. The genetic base of cultivated soybeans could be widened through the use of exotic species. In addition, exotic species may possess such key traits as disease, stress, and insect resistance.

The soybean aphid, *Aphis glycines* Matsumura, was identified as a new insect pest of soybeans in 2001 and has spread to over 21 states in the United States and three Canadian provinces by 2003 (Vennette et al. *Ann Entomol Soc Am* 97:217-226 (2004)). High yields are critical to a farmer's profit margin, but soybean aphids can cause yield losses of 50% or more (Wang et al., *Plant Protect* 20:12-13 (1994)). In addition to the decrease in yield, an increase in insecticide use can also decrease a farmer's profit margin. Over 7 million acres of soybean in the North Central United States were sprayed with insecticide to control soybean aphids in 2003; the estimated cost of the insecticide treatments was between $84 and $105 million in the North Central region alone in 2003 (Landis et al. NCR-125 Arthropod biological control: state reports for 2003; Li et al., *Mol Breeding* 19:25-34 (2007)).

Soybean aphids can directly damage the plant by removing significant amounts of water and nutrients, causing the leaves to yellow and wilt. Additionally, aphids excrete honeydew, a sugar-rich sticky substance, onto the leaves and plants. Honeydew often leads to the development of sooty mold, which affects photosynthesis and results in significant yield losses (Gomez et al., *Environ Exp Bot* 55: 77-86 (2006)). Soybean aphids vector a number of viruses that can stunt plant growth, distort leaves, cause mottling of leaves and stem, reduce pod numbers, and cause discoloration in the seed. Viruses transmitted via soybean aphids include soybean mosaic virus, yellow mosaic virus, tobacco etch virus, and tobacco vein mottling virus (Wang et al. *Plant Dis* 90: 920-926 (2006)).

Aphid resistance genes, such as Rag1, have been identified in the soybean variety Dowling and mapped to linkage group M (U.S. patent application Ser. No. 11/158,307, issued as U.S. Pat. No. 7,994,389, both of which are incorporated by reference herein in their entireties). Additionally, quantitative trait locus (QTL) associated with aphid resistance were identified in Plant Introduction (PI) 567598B and mapped linkage groups B2, D1b, J and K (PCT Patent Application No. PCT/US2006/019200, incorporated by reference herein in its entirety). Aphid resistance from Dowling and PI 567598B has been effective against specific populations of aphids in certain geographies, but the resistance has broken down in broader aphid populations and geographies.

The present inventors have discovered that various biotypes of soybean aphid exist and can now be classified according to the methods of the present invention. A biotype is typically described as a population of a species of organisms having differentiable physiologic characteristics, such as response to a native resistance gene or resistance locus. The soybean variety 'Dowling' was described in 2004 as being resistant to soybean aphids and containing the Rag1 QTL for resistance. Within two years, a biotype of soybean aphid in Ohio was reported to overcome Rag1 resistance (Kim et al. *Crop Sci* 48:923-928 (2008)). This soybean aphid has not been characterized and there are currently no reports on the number of soybean aphid biotypes in the United States.

BRIEF SUMMARY OF THE INVENTION

The invention, in an embodiment, is directed to a method of characterizing a soybean aphid biotype comprising: providing at least two soybean plants, wherein the soybean plants have soybean aphid resistance alleles that are different from one another; exposing each soybean plant to a soybean aphid population to elicit an aphid response; measuring the response of said aphid population; and characterizing said aphid population as a biotype based on the response of the aphid population to said plants.

In another embodiment, the invention is direct to a method of evaluating soybean plants for soybean aphid biotype resistance comprising: providing a first panel of soybean plants, wherein the first panel comprises at least two soybean plants having soybean aphid resistance alleles that are different from one another; exposing each soybean plant within said panel to a soybean aphid population; measuring the response of said aphid population; characterizing said aphid population as a biotype based on the response of the aphid population to said plants; providing a second panel of soybean plants; exposing said second panel of soybean plants to at least one categorized soybean aphid biotype; and determining the level of soybean aphid resistance in said second panel of plants based upon the response of said second panel of plants to said aphid biotypes.

In still another embodiment, the invention is directed to a method for generating a soybean plant having at least partial resistance to a soybean aphid population in a given location, the method comprising: exposing said aphid population to at least two soybean plants, wherein the soybean plants have soybean aphid resistance alleles that are different from one another; identifying resistance alleles that provide at least partial resistance to said aphid population by measuring the response of said aphid population to said soybean plants; and generating a progeny soybean plant comprising the identified resistance alleles, wherein the progeny soybean plant is at least partially resistant to said soybean aphid population when grown in the given location.

In a further embodiment, the invention is directed to a method of maintaining the too biodiversity of soybean aphid biotypes from particular locations under laboratory conditions, the method comprising: collecting soybean aphids from a particular location; providing at least two soybean plants, wherein the first panel comprises at least two soybean plants having soybean aphid resistance alleles that are different from one another; exposing each soybean plant within said panel to the soybean aphids from the particular geography to elicit an aphid response; measuring the response of said aphid population; characterizing said aphid population as a biotype based on the response of the aphid population to said plants; and reproducing said soybean aphid biotype in a laboratory.

BRIEF DESCRIPTION OF NUCLEIC ACID SEQUENCES

SEQ ID NO: 1 is a forward PCR primer for the amplification of SEQ ID NO: 47.

SEQ ID NO: 2 is a reverse PCR primer for the amplification of SEQ ID NO: 47.

SEQ ID NO: 3 is a forward PCR primer for the amplification of SEQ ID NO: 48.

SEQ ID NO: 4 is a reverse PCR primer for the amplification of SEQ ID NO: 48.

SEQ ID NO: 5 is a forward PCR primer for the amplification of SEQ ID NO: 49.

SEQ ID NO: 6 is a reverse PCR primer for the amplification of SEQ ID NO: 49.

SEQ ID NO: 7 is a forward PCR primer for the amplification of SEQ ID NO: 50.

SEQ ID NO: 8 is a reverse PCR primer for the amplification of SEQ ID NO: 50.

SEQ ID NO: 9 is a forward PCR primer for the amplification of SEQ ID NO: 51.

SEQ ID NO: 10 is a reverse PCR primer for the amplification of SEQ ID NO: 51.

SEQ ID NO: 11 is a forward PCR primer for the amplification of SEQ ID NO: 52.

SEQ ID NO: 12 is a reverse PCR primer for the amplification of SEQ ID NO: 52.

SEQ ID NO: 13 is a forward PCR primer for the amplification of SEQ ID NO: 53.

SEQ ID NO: 14 is a reverse PCR primer for the amplification of SEQ ID NO: 53.

SEQ ID NO: 15 is a forward PCR primer for the amplification of SEQ ID NO: 54.

SEQ ID NO: 16 is a reverse PCR primer for the amplification of SEQ ID NO: 54.

SEQ ID NO: 17 is a forward PCR primer for the amplification of SEQ ID NO: 55.

SEQ ID NO: 18 is a reverse PCR primer for the amplification of SEQ ID NO: 55.

SEQ ID NO: 19 is a forward PCR primer for the amplification of SEQ ID NO: 56.

SEQ ID NO: 20 is a reverse PCR primer for the amplification of SEQ ID NO: 56.

SEQ ID NO: 21 is a forward PCR primer for the amplification of SEQ ID NO: 57.

SEQ ID NO: 22 is a reverse PCR primer for the amplification of SEQ ID NO: 57.

SEQ ID NO: 23 is a forward PCR primer for the amplification of SEQ ID NO: 58.

SEQ ID NO: 24 is a reverse PCR primer for the amplification of SEQ ID NO: 58.

SEQ ID NO: 25 is a forward PCR primer for the amplification of SEQ ID NO: 59.

SEQ ID NO: 26 is a reverse PCR primer for the amplification of SEQ ID NO: 59.

SEQ ID NO: 27 is a forward PCR primer for the amplification of SEQ ID NO: 60.

SEQ ID NO: 28 is a reverse PCR primer for the amplification of SEQ ID NO: 60.

SEQ ID NO: 29 is a forward PCR primer for the amplification of SEQ ID NO: 61.

SEQ ID NO: 30 is a reverse PCR primer for the amplification of SEQ ID NO: 61.

SEQ ID NO: 31 is a forward PCR primer for the amplification of SEQ ID NO: 62.

SEQ ID NO: 32 is a reverse PCR primer for the amplification of SEQ ID NO: 62.

SEQ ID NO: 33 is a forward PCR primer for the amplification of SEQ ID NO: 63.

SEQ ID NO: 34 is a reverse PCR primer for the amplification of SEQ ID NO: 63.

SEQ ID NO: 35 is a forward PCR primer for the amplification of SEQ ID NO: 64.

SEQ ID NO: 36 is a reverse PCR primer for the amplification of SEQ ID NO: 64.

SEQ ID NO: 37 is a forward PCR primer for the amplification of SEQ ID NO: 65.

SEQ ID NO: 38 is a reverse PCR primer for the amplification of SEQ ID NO: 65.

SEQ ID NO: 39 is a forward PCR primer for the amplification of SEQ ID NO: 66.

SEQ ID NO: 40 is a reverse PCR primer for the amplification of SEQ ID NO: 66.

SEQ ID NO: 41 is a forward PCR primer for the amplification of SEQ ID NO: 67.

SEQ ID NO: 42 is a reverse PCR primer for the amplification of SEQ ID NO: 67.

SEQ ID NO: 43 is a forward PCR primer for the amplification of SEQ ID NO: 68.

SEQ ID NO: 44 is a reverse PCR primer for the amplification of SEQ ID NO: 68.

SEQ ID NO: 45 is a forward PCR primer for the amplification of SEQ ID NO: 69.

SEQ ID NO: 46 is a reverse PCR primer for the amplification of SEQ ID NO: 69.

SEQ ID NO: 47 is a genomic sequence derived from *Glycine Max* corresponding to aphid resistance locus 1.

SEQ ID NO: 48 is an alternate genomic sequence derived from *Glycine Max* corresponding to aphid resistance locus 1.

SEQ ID NO: 49 is a genomic sequence derived from *Glycine Max* corresponding to aphid resistance locus 2.

SEQ ID NO: 50 is an alternate genomic sequence derived from *Glycine Max* corresponding to aphid resistance locus 2.

SEQ ID NO: 51 is another alternate genomic sequence derived from *Glycine Max corresponding to aphid resistance locus* 2.

SEQ ID NO: 52 is yet another alternate genomic sequence derived from *Glycine Max* corresponding to aphid resistance locus 2.

SEQ ID NO: 53 is still another alternate genomic sequence derived from *Glycine Max* corresponding to aphid resistance locus 2.

SEQ ID NO: 54 is a genomic sequence derived from *Glycine Max* corresponding to aphid resistance locus 3.

SEQ ID NO: 55 is an alternate genomic sequence derived from *Glycine Max* corresponding to aphid resistance locus 3.

SEQ ID NO: 56 is an alternate genomic sequence derived from *Glycine Max corresponding to aphid resistance locus* 3.

SEQ ID NO: 57 is an alternate genomic sequence derived from *Glycine Max* corresponding to aphid resistance locus 3.

SEQ ID NO: 58 is an alternate genomic sequence derived from *Glycine Max* corresponding to aphid resistance locus 3.

SEQ ID NO: 59 is an alternate genomic sequence derived from *Glycine Max* corresponding to aphid resistance locus 3.

SEQ ID NO: 60 is an alternate genomic sequence derived from *Glycine Max* corresponding to aphid resistance locus 3.

SEQ ID NO: 61 is an alternate genomic sequence derived from *Glycine Max corresponding to aphid resistance locus* 3.

SEQ ID NO: 62 is an alternate genomic sequence derived from *Glycine Max* corresponding to aphid resistance locus 3.

SEQ ID NO: 63 is an alternate genomic sequence derived from *Glycine Max* corresponding to aphid resistance locus 3.

SEQ ID NO: 64 is an alternate genomic sequence derived from *Glycine Max* corresponding to aphid resistance locus 3.

SEQ ID NO: 65 is an alternate genomic sequence derived from *Glycine Max* corresponding to aphid resistance locus 3.

SEQ ID NO: 66 is an alternate genomic sequence derived from *Glycine Max corresponding to aphid resistance locus* 3.

SEQ ID NO: 67 is an alternate genomic sequence derived from *Glycine Max* corresponding to aphid resistance locus 3.

SEQ ID NO: 68 is an alternate genomic sequence derived from *Glycine Max* corresponding to aphid resistance locus 3.

SEQ ID NO: 69 is an alternate genomic sequence derived from *Glycine Max* corresponding to aphid resistance locus 3.

SEQ ID NO: 70 is a probe for the detection of the SNP of SEQ ID NO: 47.

SEQ ID NO: 71 is an alternate probe for the detection of the SNP of SEQ ID NO: 47.

SEQ ID NO: 72 is a probe for the detection of the SNP of SEQ ID NO: 48.

SEQ ID NO: 73 is an alternate probe for the detection of the SNP of SEQ ID NO: 48.

SEQ ID NO: 74 is a probe for the detection of the SNP of SEQ ID NO: 49.

SEQ ID NO: 75 is an alternate probe for the detection of the SNP of SEQ ID NO: 49.

SEQ ID NO: 76 is a probe for the detection of the SNP of SEQ ID NO: 50.

SEQ ID NO: 77 is an alternate probe for the detection of the SNP of SEQ ID NO: 50.

SEQ ID NO: 78 is a probe for the detection of the SNP of SEQ ID NO: 51.

SEQ ID NO: 79 is an alternate probe for the detection of the SNP of SEQ ID NO: 51.

SEQ ID NO: 80 is a probe for the detection of the SNP of SEQ ID NO: 52.

SEQ ID NO: 81 is an alternate probe for the detection of the SNP of SEQ ID NO: 52.

SEQ ID NO: 82 is a probe for the detection of the SNP of SEQ ID NO: 53.

SEQ ID NO: 83 is an alternate probe for the detection of the SNP of SEQ ID NO: 53.

SEQ ID NO: 84 is a probe for the detection of the SNP of SEQ ID NO: 54.

SEQ ID NO: 85 is an alternate probe for the detection of the SNP of SEQ ID NO: 54.

SEQ ID NO: 86 is a probe for the detection of the SNP of SEQ ID NO: 55.

SEQ ID NO: 87 is an alternate probe for the detection of the SNP of SEQ ID NO: 55.

SEQ ID NO: 88 is a probe for the detection of the SNP of SEQ ID NO: 56.

SEQ ID NO: 89 is an alternate probe for the detection of the SNP of SEQ ID NO: 56.

SEQ ID NO: 90 is a probe for the detection of the SNP of SEQ ID NO: 57.

SEQ ID NO: 91 is an alternate probe for the detection of the SNP of SEQ ID NO: 57.

SEQ ID NO: 92 is a probe for the detection of the SNP of SEQ ID NO: 58.

SEQ ID NO: 93 is an alternate probe for the detection of the SNP of SEQ ID NO: 58.

SEQ ID NO: 94 is a probe for the detection of the SNP of SEQ ID NO: 59.

SEQ ID NO: 95 is an alternate probe for the detection of the SNP of SEQ ID NO: 59.

SEQ ID NO: 96 is a probe for the detection of the SNP of SEQ ID NO: 60.

SEQ ID NO: 97 is an alternate probe for the detection of the SNP of SEQ ID NO: 60.

SEQ ID NO: 98 is a probe for the detection of the SNP of SEQ ID NO: 61.

SEQ ID NO: 99 is an alternate probe for the detection of the SNP of SEQ ID NO: 61.

SEQ ID NO: 100 is a probe for the detection of the SNP of SEQ ID NO: 62.

SEQ ID NO: 101 is an alternate probe for the detection of the SNP of SEQ ID NO: 62.

SEQ ID NO: 102 is a probe for the detection of the SNP of SEQ ID NO: 63.

SEQ ID NO: 103 is an alternate probe for the detection of the SNP of SEQ ID NO: 63.

SEQ ID NO: 104 is a probe for the detection of the SNP of SEQ ID NO: 64.

SEQ ID NO: 105 is an alternate probe for the detection of the SNP of SEQ ID NO: 64.

SEQ ID NO: 106 is a probe for the detection of the SNP of SEQ ID NO: 65.

SEQ ID NO: 107 is an alternate probe for the detection of the SNP of SEQ ID NO: 65.

SEQ ID NO: 108 is a probe for the detection of the SNP of SEQ ID NO: 66.

SEQ ID NO: 109 is an alternate probe for the detection of the SNP of SEQ ID NO: 66.

SEQ ID NO: 110 is a probe for the detection of the SNP of SEQ ID NO: 67.

SEQ ID NO: 111 is an alternate probe for the detection of the SNP of SEQ ID NO: 67.

SEQ ID NO: 112 is a probe for the detection of the SNP of SEQ ID NO: 68.

SEQ ID NO: 113 is an alternate probe for the detection of the SNP of SEQ ID NO: 68.

SEQ ID NO: 114 is a probe for the detection of the SNP of SEQ ID NO: 69.

SEQ ID NO: 115 is an alternate probe for the detection of the SNP of SEQ ID NO: 69.

DETAILED DESCRIPTION OF THE INVENTION

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, $5^{th}$ Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed, Oxford University Press: New York, 2002; and Lewin, Genes IX, Oxford University Press: New York, 2007. The nomenclature for DNA bases as set forth at 37 CFR §1.822 is used.

An "allele" refers to an alternative sequence at a particular locus; the length of an allele can be as small as 1 nucleotide base, but is typically larger.

A "locus" is a position on a genomic sequence that is usually found by a point of reference; for example, a short DNA sequence that is a gene, or part of a gene or intergenic region. The loci of this invention comprise one or more polymorphisms in a population; for example, alternative alleles present in some individuals.

As used herein, "polymorphism" means the presence of one or more variations of a nucleic acid sequence at one or more loci in a population of one or more individuals. The variation may comprise, but is not limited to, one or more base changes, the insertion of one or more nucleotides or the deletion of one or more nucleotides. A polymorphism may arise from random processes in nucleic acid replication, through mutagenesis, as a result of mobile genomic elements, from copy number variation, and during the process of meiosis, such as unequal crossing over, genome duplication and chromosome breaks, and fusions. The variation can be commonly found or may exist at low frequency within a population, the commonly found variation having greater utility in general plant breeding and the low frequency variation being associated with rare but important phenotypic variation. Useful polymorphisms may include single nucleotide polymorphisms (SNPs), insertions or deletions in DNA sequence (Indels), simple sequence repeats of DNA sequence (SSRs), restriction fragment length polymorphisms (RFLPs), and tags of SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms. In addition, the presence, absence, or variation in copy number of any of the preceding may comprise polymorphisms.

As used herein, "marker" means a detectable characteristic that can be used to discriminate between organisms. Examples of such characteristics may include genetic markers, protein composition, protein levels, oil composition, oil levels, carbohydrate composition, carbohydrate levels, fatty acid composition, fatty acid levels, amino acid composition, amino acid levels, biopolymers, pharmaceuticals, starch composition, starch levels, fermentable starch, fermentation yield, fermentation efficiency, energy yield, secondary compounds, metabolites, morphological characteristics, and agronomic characteristics. As used herein, "genetic marker" means a polymorphic nucleic acid sequence or nucleic acid feature. A genetic marker may be represented by one or more particular variant sequences, or by a consensus sequence. In other words, a "genetic marker" is an isolated variant or consensus of such a sequence.

As used herein, "marker assay" means a method for detecting a polymorphism at a particular locus using a particular method; for example, measurement of at least one phenotype (such as seed color, flower color, or other visually detectable trait), restriction RFLP, single base extension, electrophoresis, sequence alignment, allelic specific oligonucleotide hybridization (ASO), random amplified polymorphic DNA (RAPD), microarray-based technologies, and nucleic acid sequencing technologies.

As used herein, "typing" refers to any method whereby the specific allelic form of a given soybean genomic polymorphism is determined. For example, a single nucleotide polymorphism (SNP) is typed by determining which nucleotide is present (for example, an A, G, T, or C). Indels are determined by determining if the Indel is present. Indels can be typed by a variety of assays including, but not limited to, marker assays.

As used herein, the phrase "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "interrogation position" refers to a physical position on a solid support that can be queried to obtain genotyping data for one or more predetermined genomic polymorphisms.

As used herein, "consensus sequence" refers to a constructed DNA sequence which identifies SNP and Indel polymorphisms in alleles at a locus. Consensus sequence can be based on either strand of DNA at the locus and states the nucleotide base of either one of each SNP in the locus and the nucleotide bases of all Indels in the locus. Thus, although a consensus sequence may not be a copy of an actual DNA sequence, a consensus sequence is useful for precisely designing primers and probes for actual polymorphisms in the locus.

As used herein, the term "single nucleotide polymorphism," also referred to by the abbreviation "SNP," means a polymorphism at a single site wherein said polymorphism constitutes a single base pair change, an insertion of one or more base pairs, or a deletion of one or more base pairs.

As used herein, the term "haplotype" means a chromosomal region within a haplotype window defined by at least one polymorphic molecular marker. The unique marker fingerprint combinations in each haplotype window define individual haplotypes for that window. Further, changes in a haplotype, brought about by recombination for example, may result in the modification of a haplotype so that it comprises only a portion of the original (parental) haplotype operably linked to the trait, for example, via physical linkage to a gene, QTL, or transgene. Any such change in a haplotype would be included in the definition of what constitutes a haplotype, so long as the functional integrity of that genomic region is unchanged or improved.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region. Each haplotype window includes at least one polymorphic molecular marker. Haplotype windows can be mapped along each chromosome in the genome. Haplotype windows are not fixed per se and, given the ever-increasing density of molecular markers, the number and size of haplotype windows may evolve, with the number of windows increasing and their respective sizes decreasing, thus resulting in an ever-increasing degree confidence in ascertaining identity by descent based on the identity by state at the marker loci.

As used herein, "genotype" means the genetic component of the phenotype and it can be indirectly characterized using markers or directly characterized by nucleic acid sequencing. Suitable markers include a phenotypic character, a metabolic profile, a genetic marker, or some other type of marker. A genotype may constitute an allele for at least one genetic marker locus or a haplotype for at least one haplotype window. In some embodiments, a genotype may represent a single locus and in others it may represent a genome-wide set of loci. In another embodiment, the genotype can reflect the sequence of a portion of a chromosome, an entire chromosome, a portion of the genome, and the entire genome.

As used herein, "phenotype" means the detectable characteristics of a cell or organism which can be influenced by gene expression.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, for example, with no linkage one quarter of the gametes will be of each genotype. Segregation of gametes into a genotypes differing from one quarter are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are said to be "genetically linked" when they are in linkage disequilibrium.

As used herein, "quantitative trait locus" (QTL) means a locus that controls to some degree numerically representable traits that are usually continuously distributed.

As used herein, "aphid" refers to any of various small, soft-bodied, plant-sucking insects of the Order Homoptera, further of the family Aphididae, wherein examples of Aphididae include, but are not limited to, the genus of *Acyrthosiphon, Allocotaphis, Amphorophora, Anoecia, Anuraphis, Aphidounguis, Aphidura, Aphis, Asiphonaphis, Astegopteryx, Aulacorthum, Betacallis, Betulaphis, Boernerina, Brachycaudus, Brachycorynella, Brevicoryne, Calaphis, Callipterinella, Callipterus, Cavariella, Cerataphis, Ceratovacuna, Chaetomyzus, Chaetosiphon, Chaitophorus, Chaitoregma, Chromaphis, Cinara, Clethrobius, Clydesmithia, Coloradoa, Cornaphis, Cryptomyzus, Crypturaphis, Doralis, Doraphis, Drepanaphis, Drepanosiphoniella, Drepanosiphum, Dysaphis, Eomacrosiphum, Epipemphigus, Ericolophium, Eriosoma, Essigella, Euceraphis, Eulachnus, Eumyzus, Eutrichosiphum, Fimbriaphis, Fullawaya, Geopemphigus, Glyphina, Gootiella, Greenidea, Grylloprociphilus, Hamamelistes, Hannabura, Hormaphis, Hyadaphis, Hyalomyzus, Hyalopterus, Hyperomyza, Hyperomyzus, Hysteroneura, Illinoia, Indiaphis, Indomasonaphis, Kakimia, Lachnus, Laingia, Lambersaphis, Latgerina, Longicaudus, Longistigma, Macromyzus, Macrosiphoniella*, while even further any one or more of the following genus species of *Aphididae*, for example, soybean aphid *Aphis glycines*, bean aphid *Aphis fabae*, cotton aphid *Aphis gossypii*, rose aphid *Macrosiphun rosae*, green peach aphid *Myzus persicae*, corn leaf aphid *Rhopalosiphum maidis*, and spotted alfalfa aphid *Therioaphis maculata*, wooly apple aphid *Eriosoma lanigerum*.

As used herein, "soybean aphid," "*Aphis glycines*," and "*Aphis glycines*" Matasamura refer to an aphid that feeds on soybean. Any aphid that is found on and feeds on a soybean plant, such as the bean aphid *Aphis fabae* is a target for aphid resistance in soybeans and is within the scope of the present invention. A soybean plant of the present invention can be resistant to one or more aphids infesting a soybean plant. In one aspect, the present invention provides plants resistant to aphids as well as methods and compositions for screening soybean plants for resistance or susceptibility to aphids of the genus *Aphis*. In another aspect, the present invention provides methods and compositions for screening soybean plants for resistance or susceptibility to *Aphis glycines*.

As used herein, "biotype" means any of a number of strains of a species of organisms having differentiable physiologic characteristics, such as responses to a native resistance gene or resistance locus.

As used herein, "resistance allele" means the isolated nucleic acid sequence that includes the polymorphic allele associated with resistance to soybean aphid.

As used herein, the term "soybean" means *Glycine max* and includes all soybean plant varieties that can be bred with soybean, including wild soybean species.

Plants of the present invention can be plants that are very resistant, resistant, substantially resistant, mid-resistant, comparatively resistant, partially resistant, mid-susceptible, or susceptible to pest infestation.

As used herein, the terms "resistant", "resistance" and "host plant resistance" refer the ability of a host plant to prevent or reduce infestation and damage of a pest from the group comprising insects, nematodes, pathogens, fungi, viruses, and diseases.

As used herein, the terms "antixenosis" or "non-preference resistance" refer to the ability of a plant to ability to repel insects, causing a reduction in egg laying and feeding.

As used herein, the term "antibiosis" refers the ability of a plant to reduce survival, growth, or reproduction of insects that feed on it.

As used herein, the term "tolerance" refers to the ability of host plant to produce a larger and higher quality yield than other plants when being fed upon by similar numbers of insects.

As used herein, the term "elite line" means any line that has resulted from breeding and selection for superior agronomic performance. Non-limiting examples of elite soybean varieties that are commercially available to farmers or soybean breeders include AG00802, A0868, AG0902, A1923, AG2403, A2824, A3704, A4324, A5404, AG5903 and AG6202 (Asgrow Seeds, Des Moines, Iowa, USA);

BPR0144RR, BPR 4077NRR and BPR 4390NRR (Bio Plant Research, Camp Point, Ill., USA); DKB17-51 and DKB37-51 (DeKalb Genetics, DeKalb, Ill., USA); DP 4546 RR, DP 7870 RR (Delta & Pine Land Company, Lubbock, Tex., USA); JG 03R501, JG 32R606C ADD and JG 55R503C (JGL Inc., Greencastle, Ind., USA); NKS13-K2 (NK Division of Syngenta Seeds, Golden Valley, Minn., USA); 90M01, 91M30, 92M33, 93M11, 94M30, 95M30 and 97B52 (Pioneer Hi-Bred International, Johnston, Iowa, USA); SG4771NRR and SG5161NRR/STS (Soygenetics, LLC, Lafayette, Ind., USA); and S00-K5, S11-L2, S28-Y2, S43-B1, S53-A1, S76-L9 and S78-G6 (Syngenta Seeds, Henderson, Ky., USA). An elite plant is a representative plant from an elite variety.

As used herein, the term "comprising" means "including but not limited to".

The present invention, in an embodiment, provides methods for categorizing aphid biotypes. The present invention also relates to methods to determine the presence or absence of aphid resistance in soybean plants, the term soybean plants herein including but not limited to exotic germplasm, populations, lines, elite lines, cultivars, and varieties. The present invention is not limited to any type of aphid resistant trait, and includes, but is not limited to antibiosis, antixenosis, and repellency of aphids. More particularly, an embodiment of the invention relates to methods for identifying the efficacy of resistance across multiple aphid biotypes. The present invention also relates, in an embodiment, to the use of multiple aphid biotypes to screen and select for aphid resistance within soybean plants. The present invention further provides, in an embodiment, information on using multiple aphid biotypes to screen for resistance and stack the resistance into a single soybean line to enhance resistance.

While the term "soybean plants" may be used herein, it is understood that the methods of the invention may be used with any type of plant known in the art. For example, the methods of the invention could be applied to corn or cotton plants or insect pests that feed thereon.

In an embodiment, the present invention provides methods for characterizing soybean aphid biotypes. The method comprises providing at least two soybean plants having soybean aphid resistance alleles that are different from one another. In some embodiments, the panel may comprise at least three soybean plants. In other embodiments, the panel may comprise at least four or more soybean plants. In a particular embodiment, each of the soybean plants in the panel has different soybean aphid resistance alleles. In another embodiment, at least one susceptible soybean plant, which has no resistance to the soybean aphid, is provided as the control.

According to a method, the soybean panel is then exposed to a soybean aphid population. The soybean aphid population may be collected from a particular geographical location or may be reproduced in a laboratory. The soybean aphid population may be collected under particular environmental conditions.

In a method of the invention, the response of the aphid population to the various soybean plants in the panel is then measured. Any measurement known in the art may be used. A plant may be assayed for aphid resistance or susceptibility by visually estimating the number of aphids on a plant (Mensah et al. *Crop Sci* 25:2228-2233 (2005)). The measurement for resistance or susceptibility may determine whether a soybean plant is very resistant, resistant, moderately resistant, moderately susceptible, or susceptible. As used herein, "aphid resistance" refers to preventing or inhibiting the ability of aphids to cause damage, such as reducing feeding, delaying growth and developing, and/or reducing fecundity to a host plant.

In another embodiment, the aphid response to a particular soybean plant may be fecundity or mortality. In yet another aspect of the invention, the soybean plant can show a comparative resistance compared to a non-resistant control soybean plant. In this aspect, a control soybean plant may be genetically similar except for the aphid resistant allele or alleles in question. Such plants can be grown under similar conditions with equivalent or near equivalent exposure to the pest. In this aspect, the resistant plant, or plants, has significantly fewer aphids per plant or damage per plant compared to known susceptible plants, or an equivalent or reduced number of aphids or damage per plant compared to known resistant plants.

Finally, the method of the invention may involve characterizing the aphid population as a biotype based on the response of the aphid population to the plants.

In another embodiment, the invention is directed to a method of evaluating soybean plants for aphid biotype resistance. In this embodiment, at least one aphid biotype is first characterized according to the above method. A second panel of soybean plants is then exposed to at least one categorized soybean aphid biotype and the level of soybean aphid resistance in the second panel of plants is determined based upon the response of the second panel of plants to said aphid biotypes. In some embodiments, the second panel of soybean plants comprises plants which are different from those provided in the first panel. In a particular embodiment, the second panel of soybean plants comprises plants having an unknown resistance to particular biotypes of soybean aphids.

In still another embodiment, the invention is directed to a method for producing a soybean plant having at least partial resistance to a soybean aphid biotype. In this method, an aphid population from a given location may be exposed to at least two soybean plants, wherein the soybean plants have soybean aphid resistance alleles that are different from one another. As used herein, the term "location" may refer to a geographical location of varying size. For example, a location may refer to a particular tract of land, city, state, or region. The method of the invention may involve then identifying resistance alleles that provide at least partial resistance to the aphid population by measuring the response of said aphid population to said soybean plants. Finally, the method may include the generation of at least one progeny soybean plant comprising the identified resistance alleles, wherein the progeny soybean plant is at least partially resistant to the soybean aphid population when grown in the given location.

In this method, the exposure and identification of resistance alleles may be conducted in the given location or may be conducted on a site, such as a laboratory, which is separate from the given location. The soybean plant which is generated according to the invention may be generated by introgressing the identified alleles from a source plant into an elite germplasm for the given location using marker-assisted breeding. In some embodiments, the source plant is different from the plants used in the exposure step of the method.

In yet another embodiment, the invention is directed to a method for producing a soybean plant having at least partial resistance to a soybean aphid biotype, the method comprising: providing at least two soybean plants, wherein the first panel comprises at least two soybean plants having soybean aphid resistance alleles that are different from one another; exposing each soybean plant within said panel to a soybean aphid population to elicit an aphid response; measuring the response of said aphid population; characterizing said aphid population as a biotype based on the response of the aphid population to said plants; identifying at least one parent soybean plant having resistance to said characterized aphid biotype; and generating at least one progeny soybean plant from said resistant parent soybean plant, wherein the progeny soybean plant has resistance to said characterized aphid biotype.

The generation of the progeny plant may be accomplished using any method known in the art and/or discussed herein. As an example, the generating step may include identifying alleles at QTL in the parent plant which confer aphid biotype resistance and transforming plant materials from the parent soybean plant with a transgenic construct that confers said identified alleles at QTL in the parent to the at least one progeny soybean plant. In another embodiment, the generating step may comprise crossing the parent soybean plant with a second soybean plant which does not have resistance to said aphid biotype to form the progeny soybean plant. In an aspect, the second soybean plant may have a desired trait and, after breeding, the progeny soybean plant has resistance to the characterized aphid biotype and has the desired trait. In still another embodiment, the generating step may comprise crossing at least one parent soybean plant with at least one second soybean plant which does not have resistance to said aphid biotype in order to form a segregating population; screening the segregating population with at least one nucleic acid marker to determine if one or more soybean plants from the segregating population contains the aphid biotype resistance; and selecting from the segregation population one or more soybean plants containing the aphid biotype resistance.

In a still further embodiment, the invention is directed to a method of maintaining the biodiversity of aphid biotypes. In this embodiment, at least one aphid biotype is first characterized according to the above method and is then reproduced in a laboratory. The aphid biotype may be reproduced a number of times.

In other embodiments, the present invention relates to methods to determine the presence or absence of favorable alleles at QTL conferring aphid resistance in soybean plants. More particularly, the invention relates to methods for identifying molecular markers associated with aphid resistance QTL. The present invention also relates to the use of molecular markers to screen and select for aphid resistance within soybean plants. The present invention further provides information on using the molecular markers associated with more than one aphid resistance QTL to stack the resistance into a single soybean line to enhance resistance.

In an embodiment, the present invention provides QTL associated with resistance to one or more of arthropods including, but not limited to, Coleoptera, for example, *Cerotoma* sp. such as bean leaf beetle (*Cerotoma trifurcata*), *Diabrotica* sp. such as spotted cucumber beetle (*Diabrotica undecimpunctata howardi*), *Epicauta* sp. such as blister beetle (*Epicauta pestifera*), *Popilli* sp. such as Japanese beetle (*Popillia japonica*), *Dectes* sp. such as soybean stem borer (*Dectes texanus texanus*), *Colaspis* sp. such as grape *colaspis* (*Colaspis brunnea*); Orthoptera, for example, *Melanoplus* sp. such as red-legged grasshopper (*Melanoplus femurrubrum*), *Shistocerca* sp. such as American locust (*Shistocerca Americana*); Lepidoptera, for example, *Plathypen* sp. such as green cloverworm (*Plathypena scabra*), *Pseudoplusia* sp. such as soybean looper (*Pseudoplusia includens*), *Anticarsia* sp. such as velvetbean caterpillar (*Anticarsia gemmatalis*), *Epargyreus* sp. such as Silverspotted skipper (*Epargyreus clarus*), *Estigmene* sp. such as saltmarsh caterpillar (*Estigmene acrea*), *Spodoptera* sp. such as beet armyworm (*Spodoptera exigua*), *Heliothis* sp. such as corn earworm (*Heliothis zea*), *Matsumuraeses* sp. such as bean podworm (*Matsumuraeses phaseoli*); Hemiptera, for example, *Acrosternum* sp. such as green stink bugs (*Acrosternum hilare*), *Euschistus* sp. such as brown stink bug (*Euschistus servus*), *Nezara* sp. such as southern stinkbug (*Nezara viridula*); Homoptera, for example, *Spissistilus* sp. such as three-cornered alfalfa hopper (*Spissistilus festinus*), *Aphis* sp. such as soybean aphid (*Aphis glycines*); and Thysanoptera, for example, *Sericothrips* sp. such as soybean thrips (*Sericothrips variabilis*).

In another embodiment, the present invention provides loci associated with resistance to nematodes including, but not limited to, *Heterodera* sp. such as soybean cyst nematode (*Heterodera glycines*), *Belonolaimus* sp. such as sting nematode (*Belonolaimus longicaudatus*), *Rotylenchulus* sp. such as reniform nematode (*Rotylenchulus reniformis*), *Meloidogyne* sp. such as southern root-knot nematode (*Meloidogyne incognita*), peanut root-knot nematode (*Meloidogyne arenaria*) and the Javanese root-knot nematode (*Meloidogyne javanica*).

In certain embodiments, the present invention includes a method of introgressing more than one aphid resistant locus into a soybean plant by (A) crossing at least one first soybean plant comprising a nucleic acid sequence selected from the group comprising of SEQ ID NO: 47 through SEQ ID NO: 69 with at least one second soybean plant in order to form a segregating population, (B) screening the segregating population with one or more nucleic acid markers to determine if one or more soybean plants from the segregating population contains the nucleic acid sequence, and (C) selecting from the segregation population one or more soybean plants comprising a nucleic acid sequence selected from the group comprising of SEQ ID NO: 47 through SEQ ID NO: 69.

In other embodiments, the present invention includes a method of introgressing an allele into a soybean plant comprising: (A) crossing at least one aphid resistant soybean plant with at least one soybean plant in order to form a segregating population; (B) screening the segregating population with two or more nucleic acid markers to determine if one or more soybean plants from the segregating population contains two or more aphid resistant alleles, wherein said aphid resistance allele is an allele selected from the group comprising of aphid resistance allele 1, aphid resistance allele 2, and aphid resistance allele 3.

In still other embodiments, the present invention includes an elite soybean plant comprising a nucleic acid sequence selected from the group comprising of SEQ ID NO: 47 through SEQ ID NO: 69. In a further embodiment, the present invention includes an elite soybean plant with enhanced aphids resistance comprising a nucleic acid sequence selected from the group comprising of SEQ ID NO: 47 through SEQ ID NO: 69.

An aphid resistance allele of the present invention may be introduced into a soybean line comprising one or more transgenes conferring transgenic plant that contains one or more genes for herbicide tolerance, increased yield, insect control, fungal disease resistance, virus resistance, nematode resistance, bacterial disease resistance, mycoplasma disease resistance, modified oils production, high oil production, high protein production, germination and seedling growth control, enhanced animal and human nutrition, low raffinose, environmental stress resistance, increased digestibility, production of industrial enzymes, pharmaceutical proteins, peptides and small molecules, improved processing traits, improved flavor, increased nitrogen fixation, hybrid seed production, reduced allergenicity, and/or modification for increased suitability for biopolymer or biofuel production. These agronomic traits can be provided by the methods of plant biotechnology in the form of transgenes in soybean.

A number of molecular genetic maps of *Glycine* have been reported (Mansur et al., *Crop Sci.* 36: 1327-1336 (1996), Shoemaker et al., *Genetics* 144: 329-338 (1996); Shoemaker et al., *Crop Science* 32: 1091-1098 (1992), Shoemaker et al., *Crop Science* 35: 436-446 (1995); Tinley and Rafalski, *J. Cell Biochem. Suppl.* 14E: 291 (1990),); Cregan et al., *Crop Science* 39:1464-1490 (1999). *Glycine max, Glycine soja* and *Glycine max* x. *Glycine soja* share linkage groups (Shoemaker et al., *Genetics* 144: 329-338 (1996). A linkage group (LG) is a set of genes that tend to be inherited together from generation to generation. As used herein, reference to the linkage groups (LG), J, E, B1, N, A1, D1a_Q, H, D1, F, I, D1b+W, O, C1 and B2 of *Glycine max* refers to the linkage group that corresponds to linkage groups, J, E, B1, N, A1, D1a_Q, H, D1, F, I D1b+W, O, C1 and B2 from the genetic map of *Glycine max* (Mansur et al., *Crop Science* 36: 1327-1336 (1996); Cregan et al., *Crop Science* 39:1464-1490 (1999), and Soybase, Agricultural Research Service, United States Department of Agriculture).

The present invention may also provide three aphid resistance loci that are located on linkage group F, J, and M in the soybean genome (Table 1). The present invention also provides for QTL alleles capable of conferring resistance to soybean aphids. These alleles are located at aphid resistance locus 1, aphid resistance locus 2, and aphid resistance locus 3.

In the present invention, aphid resistance locus 1 is located on linkage group M. SNP markers used to monitor the introgression of aphid resistance locus 1 including SEQ ID NO: 47 through SEQ ID NO: 48. The DNA sequences associated with aphid resistance locus 1 (SEQ ID NO: 47 through SEQ ID NO: 48) can be amplified using the primers indicated as SEQ ID NO: 1 through SEQ ID NO: 4 with probes indicated as SEQ ID NO: 70 through 73.

In the present invention, aphid resistance locus 2 is located on linkage group F. SNP markers used to monitor the introgression of aphid resistance locus 2 including SEQ ID NO: 49 through SEQ ID NO: 53. The DNA sequences associated with aphid resistance locus 2 (SEQ ID NO: 49 through SEQ ID NO: 53) can be amplified using the primers indicated as SEQ ID NO: 5 through SEQ ID NO: 14, with probes indicated as SEQ ID NO: 74 through SEQ ID NO: 83.

In the present invention, aphid resistance locus 3 is located on linkage group J. SNP markers used to monitor the introgression of aphid resistance locus 3 including SEQ ID NO: 54 through SEQ ID NO: 69. The DNA sequences associated with aphid resistance locus 3 (SEQ ID NO: 54 through SEQ ID NO: 69) can be amplified using the primers indicated as SEQ ID NO: 15 through SEQ ID NO: 46, with probes indicated as SEQ ID NO: 84 through 115.

The present invention also provides a soybean plant comprising a nucleic acid sequence selected from the group comprising of SEQ ID NO: 47 through SEQ ID NO: 69 and complements thereof. In one aspect, the soybean plant comprises 1, 2, or 3 nucleic acid sequences selected from the group comprising of SEQ ID NO: 47 through SEQ ID NO: 69, fragments thereof, and complements thereof.

The present invention may also provide a soybean plant comprising 1, 2, or 3 aphid resistance loci where one or more alleles at one or more of loci are selected from the group comprising of aphid resistance allele 1, aphid resistance allele 2, and aphid resistance allele 3. Such alleles may be homozygous or heterozygous.

A resistance QTL of the present invention may be introduced into an elite soybean line. Herein, "line" refers to a group of individual plants from the similar parentage with similar traits. As noted above, an "elite line" is any line that has resulted from breeding and selection for superior agronomic performance. Additionally, an elite line is sufficiently homogenous and homozygous to be used for commercial production. Elite lines may be used in the further breeding efforts to develop new elite lines.

An aphid resistant QTL allele or alleles can be introduced from any plant that contains that allele (donor) to any recipient soybean plant. In one aspect, the recipient soybean plant can contain additional aphid resistant loci. In another aspect, the recipient soybean plant can contain a transgene. In another aspect, while maintaining the introduced QTL, the genetic contribution of the plant providing the aphid resistant QTL can be reduced by back-crossing or other suitable approaches. In one aspect, the nuclear genetic material derived from the donor material in the soybean plant can be less than or about 50% of the total genetic material, less than or about 25 of the total genetic material %, less than or about 13% of the total genetic material, less than or about 5% of the total genetic material, 3% of the total genetic material, 2% of the total genetic material or 1% of the total genetic material, but that genetic material contains the aphid resistant locus or loci of interest.

Plants containing one or more aphid resistant loci can be described as donor plants. Aphid plants containing resistant loci can be, for example, selected by using a nucleic acid molecule capable of detecting a marker polymorphism associated with resistance. In one aspect, donor plants are from the cultivar Dowling (PI 548663) or Jackson (PI 548657). In one aspect, a donor plant is the source for aphid resistance locus 1. In another aspect, a donor plant is the soybean line PI 230977. In another aspect, a donor plant is the source for aphid resistance locus 2. In one aspect, a donor plant is PI 594427C. In an aspect, a donor plant is the source for aphid resistance loci 2 and 3. In another aspect, a donor plant is the soybean line PI 567598B. In another aspect, a donor plant is the source for aphid resistance locus 3. A donor plant can be a susceptible line. In one aspect, a donor plant can also be a recipient soybean plant.

It is further understood that a soybean plant of the present invention may exhibit the characteristics of any relative maturity group. In an aspect, the maturity group is selected from the group consisting of maturity group 000, maturity group 00, maturity group 0, maturity group 1, maturity group 2, maturity group 3, maturity group 4, maturity group 5, maturity group 6, maturity group 7, maturity group 8, maturity group 9, and maturity group 10.

In another embodiment, the invention is directed to parts of the plants of the present invention. Plant parts, without limitation, include seed, endosperm, ovule and pollen. In a particular aspect of the present invention, the plant part is a seed.

The present invention also provides a container of aphid-resistant soybean seeds in which greater than 50%, 60%, 70%, 80%, 90%, 95%, or 99% of the seeds comprise 1, 2, or 3 aphid resistant loci and where one or more alleles at one or more of their loci are selected from the group consisting of aphid resistant allele 1, aphid resistant allele 2, and aphid resistant allele 3.

A container of aphid-resistant seeds can contain any number, weight, or volume of seeds. For example, a container can contain at least, or greater than, about 10, 25, 50, 100, 200, 300, 400, 500, 600, 700, 80, 90, 1000, 1500, 2000, 2500, 3000, 3500, 4000 or more seeds. In another aspect, a container can contain about, or greater than about, 1 gram, 5 grams, 10 grams, 15 grams, 20 grams, 25 grams, 50 grams, 100 grams, 250 grams, 500 grams, or 1000 grams of seeds. Alternatively, the container can contain at least, or greater than, about 0 ounces, 1 ounce, 5 ounces, 10 ounces, 1 pound, 2 pounds, 3 pounds, 4 pounds, 5 pounds, 10 pounds, 15 pounds, 20 pounds, 25 pounds, or 50 pounds or more seeds.

Containers of aphid-resistant seeds can be any container available in the art. For example, a container can be a box, a bag, a can, a packet, a pouch, a tape roll, a pail, or a tube.

In another aspect, the seeds in the containers can be treated or untreated aphid-resistant seeds. In one aspect, the seeds can be treated to improve germination, for example, by priming the seeds, or by disinfection to protect against seed-born pathogens. In another aspect, seeds can be coated with any available coating to improve, for example, plantability, seed emergence, and protection against seed-born pathogens. Seed coatings can be any form of seed coating including, but not limited to, pelleting, film coating, and encrustments.

Plants or parts thereof of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use a variety of tissue or cell types as the starting material. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., *Plant Science Letters*, 19: 193-201 (1980); Cheng et al., *Plant Science Letters*, 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

The present invention may also provide an aphid-resistant soybean plant selected for by screening for aphid resistance or susceptibility in the soybean plant, the selection comprising screening with multiple aphid biotypes.

The present invention may include a method of characterizing soybean aphid biotype comprising: (A) identifying a panel of indicator soybean plants containing novel aphid resistance alleles; (B) subjecting an aphid population to each soybean plant within said panel in a no-choice assay; (C) measuring the aphid response of said aphid population; (D) categorizing said aphid population as biotype class based on the aphid response on the indicator plants. The indicator plants may be selected from the group comprising PI 567598B, PI 200538, PI 230977, PI 594427C, Dowling, and Jackson. A no-choice assay involves restricting aphid movement to a particular host.

The present invention also provides an aphid-resistant soybean plant selected for by screening for aphid resistance or susceptibility in the soybean plant, the selection comprising interrogating genomic nucleic acids for the presence of a marker molecule that is genetically linked to an allele of a QTL associated with aphid resistance in the soybean plant.

The present invention includes a method of introgressing an aphid resistant allele into a soybean plant comprising (A) crossing at least one first soybean plant comprising a nucleic acid sequence selected from the group comprising SEQ ID NO: 47 through SEQ ID NO: 69 with at least one second soybean plant in order to form a segregating population, (B) screening the segregating population with two or more nucleic acid markers to determine if one or more soybean plants from the segregating population contains the nucleic acid sequence, and (C) selecting from the segregation population one or more soybean plants comprising a nucleic acid sequence selected from the group comprising of SEQ ID NO: 47 through SEQ ID NO: 69.

The present invention includes a method of introgressing an allele into a soybean plant comprising: (A) crossing at least one aphid resistant soybean plant with at least one aphid sensitive soybean plant in order to form a segregating population; (B) screening said segregating population with one or more nucleic acid markers to determine if one or more soybean plants from said segregating population contains two or more aphid resistant alleles, wherein said aphid resistance allele is an allele selected from the group comprising of aphid resistance allele 1, aphid resistance allele 2, and aphid resistance allele 3.

In some embodiments, the present invention includes nucleic acid molecules. Such molecules include those nucleic acid molecules capable of detecting a polymorphism genetically or physically linked to aphid resistance loci. Such molecules can be referred to as markers. Additional markers can be obtained that are linked to aphid resistance locus 1, aphid resistance locus 2, and aphid resistance locus 3 by available techniques. In one aspect, the nucleic acid molecule is capable of detecting the presence or absence of a marker located less than 50, 40, 30, 20, 10, 5, 2, or 1 centimorgans from an aphid resistance loci. In another aspect, a marker exhibits a LOD score of 2 or greater, 3 or greater, or 4 or greater, with higher numbers meaning a greater correlation with aphid resistance, as measured using MapManager or QGene Version 3 and default parameters. In another aspect, the nucleic acid molecule is capable of detecting a marker in a locus selected from the group aphid resistance locus 1, aphid resistance locus 2, and aphid resistance locus 3. In a further aspect, a nucleic acid molecule may be selected from the group comprising of SEQ ID NO: 47 through SEQ ID NO: 69, fragments thereof, complements thereof, and nucleic acid molecules capable of specifically hybridizing to one or more of these nucleic acid molecules.

In an aspect, a nucleic acid molecule of the present invention includes those that will specifically hybridize to one or more of the nucleic acid molecules set forth in SEQ ID NO: 47 through SEQ ID NO: 69 or complements thereof or fragments of either under moderately stringent conditions, for example at about 2.0×SSC and about 65° C. In a particular aspect, a nucleic acid of the present invention will specifically hybridize to one or more of the nucleic acid molecules set forth in SEQ ID NO: 47 through SEQ ID NO: 69 or complements or fragments of either under high stringency conditions. In one aspect of the present invention, a marker nucleic acid molecule of the present invention has the nucleic acid sequence set forth in SEQ ID NO: 47 through SEQ ID NO: 69 or complements thereof or fragments of either. In another aspect of the present invention, a marker nucleic acid molecule of the present invention may share between 80% and 100% or 90% and 100% sequence identity with the nucleic acid sequence set forth in SEQ ID NO: 47 through SEQ ID NO: 69 or complement thereof or fragments of either. In a further aspect of the present invention, a marker nucleic acid molecule of the present invention may share between 95% and 100% sequence identity with the sequence set forth in SEQ ID NO: 47 through SEQ ID NO: 69 or complement thereof or fragments of either. In another aspect of the present invention, a marker nucleic acid molecule of the present invention may share between 98% and 100% sequence identity with the nucleic acid sequence set forth in SEQ ID NO: 47 through SEQ ID NO: 69 or complement thereof or fragments of either.

Nucleic acid molecules or fragments thereof are capable of specifically hybridizing to other nucleic acid molecules under certain circumstances. As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if the molecules exhibit complete complementarity. As used herein, molecules exhibit "complete complementarity" when every nucleotide of one of the molecules is complementary to a nucleotide of the other. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Conventional stringency conditions are described by Sambrook et al., In: *Molecular Cloning, A Laboratory Manual, 2nd Edition, Cold Spring Harbor Press*, Cold Spring Harbor, N.Y. (1989), and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The nucleic-acid probes and primers of the present invention can hybridize under stringent conditions to a target DNA sequence. The term "stringent hybridization conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (for example, to a particular nucleic-acid sequence of interest) by the specific hybridization procedure discussed in Sambrook et al., 1989, at 9.52-9.55. See also, Sambrook et al., 1989 at 9.47-9.52, 9.56-9.58; Kanehisa 1984 *Nucl. Acids Res.* 12: 203-213; and Wetmur et al. 1968 *J. Mol. Biol.* 31:349-370. Appropriate stringency conditions that promote DNA hybridization are, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y., 1989, 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

For example, hybridization using DNA or RNA probes or primers can be performed at 65° C. in 6×SSC, 0.5% SDS, 5×Denhardt's, 100 µg/mL nonspecific DNA (for example, sonicated salmon sperm DNA) with washing at 0.5×SSC, 0.5% SDS at 65° C., for high stringency.

It is contemplated that lower stringency hybridization conditions such as lower hybridization and/or washing temperatures can be used to identify related sequences having a lower degree of sequence similarity if specificity of binding of the probe or primer to target sequence(s) is preserved. Accordingly, the nucleotide sequences of the present invention can be used for their ability to selectively form duplex molecules with complementary stretches of DNA, RNA, or cDNA fragments.

A fragment of a nucleic acid molecule can be any sized fragment and illustrative fragments include fragments of nucleic acid sequences set forth in SEQ ID NO: 47 through SEQ ID NO: 69 and complements thereof. In one aspect, a fragment can be between 15 and 25, 15 and 30, 15 and 40, 15 and 50, 15 and 100, 20 and 25, 20 and 30, 20 and 40, 20 and 50, 20 and 100, 25 and 30, 25 and 40, 25 and 50, 25 and 100, 30 and 40, 30 and 50, and 30 and 100. In another aspect, the fragment can be greater than 10, 15, 20, 25, 30, 35, 40, 50, 100, or 250 nucleotides.

Additional genetic markers can be used to select plants with an allele of a QTL associated with aphid resistance of soybean of the present invention. Examples of public marker databases include, for example: Soybase, Agricultural Research Service, and United States Department of Agriculture.

A genetic marker is a DNA sequence that has a known location on a chromosome and associated with a particular trait or gene. Genetic markers associated with aphid resistance can be used to determine whether an individual plant is resistant to aphids.

Genetic markers of the present invention include "dominant" or "codominant" markers. "Codominant markers" reveal the presence of two or more alleles (two per diploid individual). "Dominant markers" reveal the presence of only a single allele. The presence of the dominant marker phenotype (for example, a band of DNA) is an indication that one allele is present in either the homozygous or heterozygous condition. The absence of the dominant marker phenotype (for example, absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

Markers, such as single sequence repeat markers (SSR), AFLP markers, RFLP markers, RAPD markers, phenotypic markers, SNPs, isozyme markers, microarray transcription profiles that are genetically linked to or correlated with alleles of a QTL of the present invention can be utilized (Walton, 1993; Burow et al. 1988). Methods to isolate such markers are known in the art.

The detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor *Symp. Quant. Biol.* 51:263-273; European Patent No. 50,424; European Patent No. 84,796; European Patent No. 258,017; European Patent No. 237,362; European Patent No. 201,184; U.S. Pat. No. 4,683,202; U.S. Pat. No. 4,582,788; and U.S. Pat. No. 4,683,194, each of which is incorporated by reference herein in its entirety), using primer pairs that are capable of hybridizing to the proximal sequences that define a polymorphism in its double-stranded form.

For the purpose of QTL mapping, the markers included may be diagnostic of origin in order for inferences to be made about subsequent populations. SNP markers are ideal for mapping because of their abundance in the genome, their ease of use, and the ability to use multiple SNP genotypes to define haplotypes. As such, SNP markers are useful for tracking and assisting introgression of QTLs, particularly in the case of haplotypes.

The genetic linkage of additional marker molecules can be established by a gene mapping model such as, without limitation, the flanking marker model reported by Lander et al. (Lander et al. 1989 *Genetics,* 121:185-199), and the interval mapping method, based on maximum likelihood methods described therein, and implemented in the software package MAPMAKER/QTL (Lincoln and Lander, *Mapping Genes Controlling Quantitative Traits Using MAPMAKER/QTL,* Whitehead Institute for Biomedical Research, Massachusetts, (1990). Additional software includes Qgene, Version 3, Department of Plant Breeding and Biometry, 266 Emerson Hall, Cornell University, Ithaca, N.Y.). Use of Qgene software may be used.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander et al. (1989), and further described by Arias and Moreno-Gonzalez, *Plant Breeding*, Hayward, Bosemark, Romagosa (eds.) Chapman & Hall, London, pp. 314-331 (1993).

Additional models can be used. Many modifications and alternative approaches to interval mapping have been reported, including the use of non-parametric methods (Kruglyak et al. 1995 *Genetics,* 139:1421-1428). Multiple regression methods or models can be also be used, in which the trait is regressed on a large number of markers (Jansen, *Biometrics in Plant Breed*, van Oijen, Jansen (eds.) Proceedings of the Ninth Meeting of the Eucarpia Section Biometrics in Plant Breeding, The Netherlands, pp. 116-124 (1994); Weber and Wricke, *Advances in Plant Breeding*, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen et al. (Jansen et al. 1994 *Genetics,* 136:1447-1455) and Zeng (Zeng 1994 *Genetics* 136:1457-1468). Generally, the use of cofactors reduces the bias and sampling error of the estimated QTL positions (Utz and Melchinger, *Biometrics in Plant Breeding*, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng 1994). These models can be extended to multi-environment experiments to analyze genotype-environment interactions (Jansen et al. 1995 *Theor. Appl. Genet.* 91:33-3).

Selection of appropriate mapping populations is used in map construction. The choice of an appropriate mapping population depends on the type of marker systems employed (Tanksley et al., *Molecular mapping in plant chromosomes. chromosome structure and function: Impact of new concepts* J. P. Gustafson and R. Appels (eds.). Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted× adapted).

An $F_2$ population is the first generation of inbreeding after the hybrid seed is produced. Usually a single $F_1$ plant is self-pollinated to generate a population segregating for all the genes in Mendelian (1:2:1) fashion. Maximum genetic information is obtained from a completely classified $F_2$ population using a codominant marker system (Mather, Measurement of Linkage in Heredity: Methuen and Co., (1938)). In the case of dominant markers, progeny tests (for example, $F_3$, $BCF_2$) are required to identify the heterozygotes, thus making it equivalent to a completely classified $F_2$ population. However, this procedure is often prohibitive because of the cost and time involved in progeny testing. Progeny testing of $F_2$ individuals is often used in map construction where phenotypes do not consistently reflect genotype (for example, pest resistance) or where trait expression is controlled by a QTL. Segregation data from progeny test populations (for example, $F_3$ or $BCF_2$) can be used in map construction. Marker-assisted selection can then be applied to cross progeny based on marker-trait map associations ($F_2$, $F_3$), where linkage groups have not been completely disassociated by recombination events (for example, maximum disequilibrium).

Recombinant inbred lines (RIL) (genetically related lines; usually $>F_5$, developed from continuously selfing $F_2$ lines towards homozygosity) can be used as a mapping population. Information obtained from dominant markers can be maximized by using RIL because all loci are homozygous or nearly so. Under conditions of tight linkage (for example, about <10% recombination), dominant and co-dominant markers evaluated in RIL populations provide more information per individual than either marker type in backcross populations (Reiter et al. 1992 *Proc. Natl. Acad. Sci. (USA)* 89:1477-1481). However, as the distance between markers becomes larger (for example, loci become more independent), the information in RIL populations decreases dramatically.

Backcross populations (for example, generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created comprising of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al. 1992). Information obtained from backcross populations using either codominant or dominant markers is less than that obtained from $F_2$ populations because one, rather than two, recombinant gametes are sampled per plant. Backcross populations, however, are more informative (at low marker saturation) when compared to RILs as the distance between linked loci increases in RIL populations (for example, about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore et al. 1991 Proc. Natl. Acad. Sci. (U.S.A.) 88:9828-9832). In BSA, two bulked DNA samples are drawn from a segregating population originating from a single cross. These bulks contain individuals that are identical for a particular trait (resistant or susceptible to particular pests) or genomic region but arbitrary at unlinked regions (for example, heterozygous). Regions unlinked to the target region will not differ between the bulked samples of many individuals in BSA.

An alternative to traditional QTL mapping involves achieving higher resolution by mapping haplotypes versus individual markers (Fan et al. 2006 Genetics 172:663-686). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are well within the skill of the ordinary practitioner in the art.

Plants of the present invention can be part of or generated from a breeding program. The choice of breeding method depends on the mode of plant reproduction, the heritability of the trait(s) being improved, and the type of cultivar used commercially (for example, $F_1$ hybrid cultivar, pureline cultivar, etc). A cultivar is a race or variety of a plant species that has been created or selected intentionally and maintained through cultivation.

Selected non-limiting approaches for breeding the plants of the present invention are set forth below. A breeding program can be enhanced using marker assisted selection (MAS) on the progeny of any cross. It is understood that nucleic acid markers of the present invention can be used in a MAS (breeding) program. It is further understood that any commercial or non-commercial cultivars can be utilized in a breeding program. Factors such as, for example, emergence vigor, vegetative vigor, stress tolerance, disease resistance, branching, flowering, seed set, seed size, seed density, standability, and threshability will generally dictate the choice.

For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection. In an aspect, a backcross or recurrent breeding program is undertaken.

The complexity of inheritance influences the choice of the breeding method. Backcross breeding can be used to transfer one or a few favorable genes for a highly heritable trait into a desirable cultivar. This approach has been used extensively for breeding disease and insect-resistant cultivars. Various recurrent selection techniques are used to improve quantitatively inherited traits controlled by numerous genes.

Breeding lines can be tested and compared to appropriate standards in environments representative of the commercial target area(s) for two or more generations. The best lines are candidates for new commercial cultivars; those still deficient in traits may be used as parents to produce new populations for further selection.

The development of new elite soybean hybrids requires the development and selection of elite inbred lines, the crossing of these lines and selection of superior hybrid crosses. The hybrid seed can be produced by manual crosses between selected male-fertile parents or by using male sterility systems. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Backcross breeding has been used to transfer genes for a simply inherited, highly heritable trait into a desirable homozygous cultivar or inbred line, which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have most attributes of the recurrent parent (for example, cultivar) and, in addition, the desirable trait transferred from the donor parent.

The single-seed descent procedure, in the strict sense, refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advancement is completed.

Descriptions of other breeding methods that are commonly used for different traits and crops can be found in one of several reference books (Allard, "Principles of Plant Breeding," John Wiley & Sons, NY, U. of CA, Davis, C A, 50-98, 1960; Simmonds, "Principles of crop improvement," Longman, Inc., NY, 369-399, 1979; Sneep and Hendriksen, "Plant breeding perspectives," Wageningen (ed), Center for Agricultural Publishing and Documentation, 1979; Fehr, In: Soybeans: Improvement, Production and Uses, 2nd Edition, Manograph., 16:249, 1987; Fehr, "Principles of variety development," Theory and Technique, (Vol. 1) and Crop Species Soybean (Vol. 2), Iowa State Univ., Macmillan Pub. Co., NY, 360-376, 1987).

It is further understood, that the present invention may provide bacterial, viral, microbial, insect, mammalian and plant cells comprising the nucleic acid molecules of the present invention.

As used herein, a "nucleic acid molecule," be it a naturally occurring molecule or otherwise may be "substantially purified," if desired, referring to a molecule separated from substantially all other molecules normally associated with it in its native state. Alternatively, a substantially purified molecule is the predominant species present in a preparation. A substantially purified molecule may be greater than 60% free, 75% free, 90% free, or 95% free from the other molecules (exclusive of solvent) present in the natural mixture. The term "substantially purified" is not intended to encompass molecules present in their native state.

The agents of the present invention may be "biologically active" with respect to either a structural attribute, such as the capacity of a nucleic acid to hybridize to another nucleic acid molecule, or the ability of a protein to be bound by an antibody (or to compete with another molecule for such binding). Alternatively, such an attribute may be catalytic, and thus involve the capacity of the agent to mediate a chemical reaction or response.

The agents of the present invention may also be recombinant. As used herein, the term recombinant means any agent (for example, DNA or peptide), that is, or results, however indirect, from human manipulation of a nucleic acid molecule.

The agents of the present invention may be labeled with reagents that facilitate detection of the agent such as fluorescent labels (Prober et al. 1987 Science 238:336-340; Albarella et al., European Patent No. 144914), chemical labels (Sheldon et al., U.S. Pat. No. 4,582,789; Albarella et al., U.S. Pat. No. 4,563,417), or modified bases (Miyoshi et al., European Patent No. 119448).

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples.

EXAMPLES

Example 1

Identifying Soybean Aphid Diversity Interactions, Geographic Interactions, and Environmental Interactions with Host Plant Resistance The soybean aphid, *Aphis glycines*, is an invasive insect pest of soybean that was first 5 reported in North America in 2000. There is currently little knowledge about the impact of soybean aphid diversity and environmental conditions on the efficacy of host plant resistance. Compositions and methods to assay for such information are critical for discovery and deployment of aphid resistance genes. QTLs associated with soybean aphid resistance have previously been identified in soybean lines PI 567598B, PI 200538, PI 594427C, Dowling, and 10 Jackson (U.S. application Ser. No. 11/158,307, U.S. App. Pub. No. 2006/0277627, U.S. App. Ser. No. 60/963,936, each of which is incorporated herein by reference in its entirety) (Table 1). In these studies, the QTLs associated with resistance were characterized based upon particular subgroups of soybean aphids and under particular environmental conditions and, therefore, may not translate to resistance for other subgroups of aphids or other environmental conditions.

In the present invention, soybean lines PI 567598B, PI 200538, PI 230977, PI 594427C, Dowling, and Jackson were exposed to various subgroups of aphids, various geographic regions (Ohio, Illinois, and Michigan) and various environmental conditions. Although the previously described QTLs did not confer resistance across all environments, they reacted similarly to individual aphid subgroups and environmental conditions regardless of the germplasm conferring resistance (Table 1).

TABLE 1

Performance of soybean aphid resistance QTLs across environments

| Resistance Loci | Source | LG | Interval (cM) | Ohio | Illinois | Michigan |
|---|---|---|---|---|---|---|
| 1 | Dowling | M | 3.1-15.1 | Susceptible | Resistant | Varies |
| 1 | Jackson | M | 3.1-15.1 | Susceptible | Resistant | Varies |
| 2 | PI 200538 | F | 62-82 | — | Resistant | Susceptible |
| 2 | PI 230977 | F | 62-82 | Resistant | Resistant | Susceptible |
| 2 | PI 594427C | F | 62-82 | Resistant | Resistant | Susceptible |
| 3 | PI 594427C | J | 28-48 | Unknown | Resistant | Resistant |
| 3 | PI 5675988 | J | 40-42 | Unknown | Resistant | Resistant |

Example 2

Enhancing Aphid Resistance

Soybean aphids can greatly impact the yield and profitability of a crop. Host plant resistance can be an effective tool to control the pest. It is highly desirable to produce varieties with durable host plant resistance due to the time required to discover and develop varieties with new resistance genes. One strategy for increasing the durability of resistance is to incorporate multiple resistance genes into a single soybean variety. If the pyramided genes have never been deployed as single genes, it is estimated that the durability of resistance could be extended for many years. However, during the process of constructing a cultivar, it is often difficult to verify the number of resistance genes that have been successfully pyramided by phenotyping. Plants with only one resistance gene can provide similar plant protection against a single biotype of soybean aphids to plants that contain three resistance genes, although the resistance of the latter may be more durable. Therefore, using multiple aphid biotypes to evaluate the plant protection provided by multiple resistance genes in a single variety may provide information on the durability and spectrum of resistance conferred by the multiple genes deployed together.

In this example, marker-assisted selection was used for gene enrichment or fixation in populations segregating at the aphid resistance loci 1, 2, and 3. Marker-assisted selection may be used to facilitate the introgression of aphid resistance loci 1, 2, and 3 into a single soybean, thereby providing resistance to various aphid subgroups under various environmental conditions. There are several mapped SNPs in the regions of aphid resistance loci 1, 2, and 3. When parents of a cross are polymorphic, they are useful for screening progeny for the aphid resistance traits. A group of markers at each loci display linkage disequilibrium (LD) with the aphid resistance alleles (Table 2). Seed is screened with polymorphic SNP markers. The genotypic and phenotypic data are compared to identify a loci associated with aphid resistance. The statistical significance of aphid resistance markers association for aphid resistance loci 1, 2, and 3 are assed using QTLCartographer software (Basten et al. 1995, Department of Statistics, North Carolina State University, Raleigh, N.C.). This analysis fits the data to the simple linear regression model:

$y=b0+b1x+e$

The results give the estimates for b0, b1 and the F statistic for each marker. Whether or not a marker is linked to a QTL is determined by evaluating whether b1 is significantly different from zero. The F statistic compares the hypothesis H0: b1=0 to an alternative H1: b1≠0. The pr(F) is a measure of how much support there is for H0. A smaller pr(F) indicates less support for H0 and thus more support for H1. Significance at the 5%, 1%, 0.1% and 0.01% levels are indicated by \*, \*\*, \*\*\* and \*\*\*\*, respectively. When two soybean lines differ for one of the aphid resistance alleles, the markers with the greater LD are the most likely to be polymorphic.

Example 4

Methods to Ensure Aphid Diversity in Laboratory Colony

Aphids have unusual and complex life cycles which allow them to build up tremendous populations in relatively short periods of time. Soybean aphids overwinter as fertilized eggs. Nymphs which hatch from these eggs become wingless females known as stem mothers. There are no males present at this time. Stem mothers reproduce without mating and their eggs are held within their bodies until they hatch so that

TABLE 2

Markers associated with aphid resistance loci

| Region | Marker | Linkage Group | Position (cM) | SEQ ID NO: FWD Primer | SEQ ID NO: RV Primer | SEQ ID NO: | Position of Polymorphism within marker sequence | SEQ ID NO: Probe 1 | Probe 1 Allele | SEQ ID NO: Probe 2 | Prob 2 allele |
|---|---|---|---|---|---|---|---|---|---|---|---|
| 1 | NS0093656 | M | 7.2 | 1 | 2 | 47 | SNP382 | 70 | T | 71 | C |
| 1 | NS0094171 | M | 19.9 | 3 | 4 | 48 | SNP78 | 72 | T | 73 | C |
| 2 | NS0092810 | F | 54.4 | 5 | 6 | 49 | SNP51 | 74 | T | 75 | A |
| 2 | NS0092712 | F | 54.4 | 7 | 8 | 50 | SNP47 | 76 | C | 77 | A |
| 2 | NS0119285 | F | 69.6 | 9 | 10 | 51 | SNP488 | 78 | G | 79 | A |
| 2 | NS0122887 | F | 89.3 | 11 | 12 | 52 | SNP260 | 80 | G | 81 | A |
| 2 | NS0124935 | F | 89.3 | 13 | 14 | 53 | SNP142 | 82 | T | 83 | C |
| 3 | NS0124450 | J | 27.2 | 15 | 16 | 54 | SNP49 | 84 | T | 85 | C |
| 3 | NS0120079 | J | 27.2 | 17 | 18 | 55 | IND124 | 86 | AAGATAT | 87 | \*\*\*\*\*\*\* |
| 3 | NS0126493 | J | 27.2 | 19 | 20 | 56 | IND444 | 88 | TAACAGCAAGATA | 89 | \*\*\*\*\*\*\*\*\*\*\*\*\* |
| 3 | NS0100189 | J | 29.4 | 21 | 22 | 57 | SNP1184 | 90 | T | 91 | A |
| 3 | NS0123735 | J | 30 | 23 | 24 | 58 | SNP811 | 92 | T | 93 | C |
| 3 | NS0094900 | J | 31.9 | 25 | 26 | 59 | SNP168 | 94 | T | 95 | C |
| 3 | NS0124882 | J | 35.1 | 27 | 28 | 60 | SNP680 | 96 | G | 97 | A |
| 3 | NS0101003 | J | 40.9 | 29 | 30 | 61 | SNP68 | 98 | T | 99 | A |
| 3 | NS0098951 | J | 40.9 | 31 | 32 | 62 | SNP172 | 100 | T | 101 | C |
| 3 | NS0115741 | J | 42.4 | 33 | 34 | 63 | SNP712 | 102 | G | 103 | A |
| 3 | NS0125096 | J | 42.5 | 35 | 36 | 64 | SNP140 | 104 | T | 105 | A |
| 3 | NS0202761 | J | 44.1 | 37 | 38 | 65 | SNP194 | 106 | T | 107 | C |
| 3 | NS0117863 | J | 44.5 | 39 | 40 | 66 | IND364 | 108 | T | 109 | \* |
| 3 | NS0122151 | J | 44.5 | 41 | 42 | 67 | SNP63 | 110 | T | 111 | A |
| 3 | NS0122726 | J | 44.8 | 43 | 44 | 68 | SNP1002 | 112 | T | 113 | A |
| 3 | NS0203169 | J | 46 | 45 | 46 | 69 | SNP71 | 114 | T | 115 | G |

Example 3

Characterizing Subgroups of Soybean Aphids

Subgroups of soybean aphids, *Aphis glycines*, were characterized by the ability to infect a given set of resistant soybean lines. A number of soybean aphids from different regions in the U.S., including Minnesota, Ohio, Illinois, Michigan, South Dakota, Ohio, were collected. A panel of resistant soybean lines, PI 567598B, PI 200538, PI 230977, PI 594427C, Dowling, and Jackson, were inoculated with each subgroup of aphids in a controlled environment. The resistance patterns of each subgroup on the panel of resistant lines were observed. The panel of resistant soybean lines was also inoculated in the original collection location to ascertain environmental impact on resistance. The resistance patterns are used to classify soybean aphids. In addition, the panel of resistant soybeans may be expanded as new resistant germplasm sources are discovered.

young are born alive. All offspring are females which soon mature and begin to reproduce in the same manner. Laboratory colonies of aphids are prone to loss of genetic diversity due to the ability to reproduce without mating. In addition, the aphid resistance expressed by the plant is influenced by the subgroup of aphids and the environment. Therefore, it is critical to understand the genetic diversity of laboratory aphid colonies to ensure the quality of resistance phenotyping.

A subsample of the laboratory aphid colony was evaluated for resistance based on the colony's response to a given panel of resistant soybean lines (PI 567598B, PI 200538, PI 230977, PI 594427C, Dowling, and Jackson). The aphids were classified by the ability of the population to reproduce on soybean lines with different aphid resistance loci. The test was conducted in monitored environments with controlled temperature and moisture conditions. After 7 days, the numbers of aphids on the panel of resistant lines was determined and compared to the number of aphids on a standard susceptible soybean line. It may be beneficial to maintain both aphid colonies resistant to all known aphid resistance loci and aphid colonies resistant to an individual aphid resistant locus. Therefore, the method was used to monitor various types of resistance within an aphid colony. The technique was performed periodically to assure the desired resistance phenotype was maintained.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

We claim:

1. A method of generating a soybean plant having at least partial resistance to a soybean aphid biotype comprising:
    a. providing at least two soybean plants, wherein the soybean plants have soybean aphid resistance alleles that are different from one another and located on different linkage groups, and wherein at least one aphid resistance allele is aphid resistance locus 2 on LG F;
    b. exposing each soybean plant to a soybean aphid population to elicit an aphid response;
    c. measuring the aphid response;
    d. characterizing said aphid population as a biotype based on the aphid response;
    e. identifying which of the resistance alleles provide at least partial resistance to said aphid biotype based on the aphid response; and
    f. generating a progeny soybean plant comprising at least two identified resistance alleles identified in step e., wherein the progeny soybean plant is at least partially resistant to said soybean aphid biotype.

2. A method of evaluating soybean plants for soybean aphid biotype resistance comprising:
    a. providing a first panel of soybean plants, wherein the first panel comprises at least two soybean plants having soybean aphid resistance alleles that are different from one another and located on different linkage groups, and wherein at least one aphid resistance allele is aphid resistance locus 2 on LG F;
    b. exposing each soybean plant within said panel to a soybean aphid population to elicit a first aphid response;
    c. measuring the first aphid response;
    d. characterizing said aphid population as a biotype based on the first aphid response;
    e. providing a second panel of soybean plants;
    f. exposing said second panel of soybean plants to at least one characterized soybean aphid biotype of step d. to elicit a second aphid response; and
    g. determining the level of soybean aphid resistance in said second panel of plants based upon the second aphid response.

3. The method of claim 2, wherein the second panel of soybean plants comprises plants which are different from those provided in the first panel.

4. A method for generating a soybean plant having at least partial resistance to a soybean aphid population, wherein the soybean aphid population is localized to a given location, the method comprising:
    a. exposing said aphid population to at least two soybean plants, wherein the soybean plants have soybean aphid resistance alleles that are different from one another and located on different linkage groups, and wherein at least one aphid resistance allele is aphid resistance locus 2 on LG F;
    b. identifying which of the resistance alleles provide at least partial resistance to said aphid population based on the aphid response; and
    c. generating a progeny soybean plant comprising at least two identified resistance alleles identified in step b., wherein the progeny soybean plant is at least partially resistant to said soybean aphid population when grown in the given location.

5. The method of claim 4, wherein the exposing step and the identifying step are conducted on a site which is not in the given location.

6. The method according to claim 4, wherein the at least two soybean plants exposed in step a. are selected from the group consisting of PI 567598B, PI 200538, PI 230977, PI 594427C, Dowling, and Jackson.

7. The method of claim 4, wherein said aphid response is fecundity or mortality.

8. The method of claim 4, wherein the generating step comprises introgressing the identified resistance alleles from a source plant into an elite germplasm for the given location using marker-assisted breeding.

9. A method of maintaining the biodiversity of soybean aphid biotypes from particular locations under laboratory conditions, the method comprising:
  a. collecting soybean aphids from a particular location;
  b. providing a panel of at least two soybean plants, wherein the at least two soybean plants have soybean aphid resistance alleles that are different from one another and located on different linkage groups, and wherein at least one aphid resistance allele is aphid resistance locus 2 on LG F;
  c. exposing each soybean plant within said panel to the soybean aphids from the particular location to elicit an aphid response;
  d. measuring the aphid response;
  e. characterizing said aphid population as a biotype based on the aphid response; and
  f. reproducing said soybean aphid biotype in a laboratory.

10. The method of claim 9 additionally comprising:
  g. providing a second panel of soybean plants;
  h. exposing said second panel of soybean plants to the laboratory-reproduced soybean aphid biotype of step f. to elicit a second aphid response; and
  i. determining the level of soybean aphid resistance in said plants based upon the second aphid response.

11. The method of claim 9 additionally comprising:
  g. identifying at least one parent soybean plant having resistance to said characterized aphid biotype; and
  h. generating at least one progeny soybean plant from said resistant parent soybean plant, wherein the progeny soybean plant has resistance to said at least one aphid biotype.

12. The method of claim 9, wherein the reproduction step is repeated at least once.

13. A method of generating a soybean plant having at least partial resistance to a soybean aphid biotype comprising:
  a. collecting soybean aphids from a particular location;
  b. providing at least two soybean plants, wherein the at least two soybean plants have soybean aphid resistance alleles that are different from one another and located on different linkage groups, and wherein at least one aphid resistance allele is aphid resistance locus 2 on LG F;
  c. exposing each soybean plant to the soybean aphids from the particular location to elicit a first aphid response;
  d. measuring the first aphid response;
  e. characterizing said aphid biotype based on the first aphid response;
  f. reproducing said soybean aphid biotype in a laboratory;
  g. exposing at least one soybean plant of step c. to the reproduced soybean aphid biotypes to elicit a second aphid response;
  h. identifying which of the resistance alleles provides at least partial resistance to said aphid biotype based on the second aphid response; and
  i. generating a progeny soybean plant comprising at least two identified resistance alleles identified in step h., wherein the progeny soybean plant is at least partially resistant to said reproduced soybean aphid biotype.

14. The method according to claim 1, wherein in addition to aphid resistance locus 2 on LG F, at least one aphid resistance allele is selected from the group consisting of aphid resistance locus 1 on LG M and aphid resistance locus 3 on LG J.

15. The method according to claim 1, wherein the at least two soybean plants in a. are selected from the group consisting of PI 567598B, PI 200538, PI 230977, PI 594427C, Dowling, and Jackson.

16. The method of claim 1, wherein said aphid response is fecundity or mortality.

17. The method of claim 1, wherein the generating step comprises introgressing the identified resistance alleles from a source plant into an elite germplasm for the given location using marker-assisted breeding.

18. The method according to claim 2, wherein in addition to aphid resistance locus 2 on LG F, at least one aphid resistance allele is selected from the group consisting of aphid resistance locus 1 on LG M and aphid resistance locus 3 on LG J.

19. The method according to claim 4, wherein in addition to aphid resistance locus 2 on LG F, at least one aphid resistance allele is selected from the group consisting of aphid resistance locus 1 on LG M and aphid resistance locus 3 on LG J.

20. The method according to claim 9, wherein in addition to aphid resistance locus 2 on LG F, at least one aphid resistance allele is selected from the group consisting of aphid resistance locus 1 on LG M and aphid resistance locus 3 on LG J.

21. The method according to claim 13, wherein in addition to aphid resistance locus 2 on LG F, at least one aphid resistance allele is selected from the group consisting of aphid resistance locus 1 on LG M and aphid resistance locus 3 on LG J.

* * * * *

```
                        SEQUENCE LISTING

<160> NUMBER OF SEQ ID NOS: 115

<210> SEQ ID NO 1
<211> LENGTH: 19
<212> TYPE: DNA
<213> ORGANISM: Artificial Sequence
<220> FEATURE:
<223> OTHER INFORMATION: synthetic primer

<400> SEQUENCE: 1
gaccgaagac gctgtgcaa                                              19

<210> SEQ ID NO 2
<211> LENGTH: 17
<212> TYPE: DNA
<213> ORGANISM: Artificial Sequence
<220> FEATURE:
<223> OTHER INFORMATION: synthetic primer

<400> SEQUENCE: 2
ccagcctccc ggacttg                                                17

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
ctttgccatc ctaatggaat caa                                         23

<210> SEQ ID NO 4
<211> LENGTH: 22
<212> TYPE: DNA
<213> ORGANISM: Artificial Sequence
<220> FEATURE:
<223> OTHER INFORMATION: synthetic primer

<400> SEQUENCE: 4
cccagttcaa caaaacaatg ca                                          22

<210> SEQ ID NO 5
<211> LENGTH: 21
<212> TYPE: DNA
<213> ORGANISM: Artificial Sequence
<220> FEATURE:
<223> OTHER INFORMATION: synthetic primer

<400> SEQUENCE: 5
```

-continued

```
ggaatctcgt tgcactgcat t                                          21

<210> SEQ ID NO 6
<211> LENGTH: 24
<212> TYPE: DNA
<213> ORGANISM: Artificial Sequence
<220> FEATURE:
<223> OTHER INFORMATION: synthetic primer

<400> SEQUENCE: 6
tgctcaagaa tctctcacaa atgg                                       24

<210> SEQ ID NO 7
<211> LENGTH: 23
<212> TYPE: DNA
<213> ORGANISM: Artificial Sequence
<220> FEATURE:
<223> OTHER INFORMATION: synthetic primer

<400> SEQUENCE: 7
tttcttggaa aggatgcaac ttg                                        23

<210> SEQ ID NO 8
<211> LENGTH: 24
<212> TYPE: DNA
<213> ORGANISM: Artificial Sequence
<220> FEATURE:
<223> OTHER INFORMATION: synthetic primer

<400> SEQUENCE: 8
gccttcaaaa ccctttctct ttct                                       24

<210> SEQ ID NO 9
<211> LENGTH: 25
<212> TYPE: DNA
<213> ORGANISM: Artificial Sequence
<220> FEATURE:
<223> OTHER INFORMATION: synthetic primer

<400> SEQUENCE: 9
tttaaaatga gccatgttga gcata                                      25

<210> SEQ ID NO 10
<211> LENGTH: 27
<212> TYPE: DNA
<213> ORGANISM: Artificial Sequence
<220> FEATURE:
<223> OTHER INFORMATION: synthetic primer

<400> SEQUENCE: 10
ttgatcctac atttcatgaa gaactca                                    27

<210> SEQ ID NO 11
<211> LENGTH: 27
<212> TYPE: DNA
<213> ORGANISM: Artificial Sequence
<220> FEATURE:
<223> OTHER INFORMATION: synthetic primer

<400> SEQUENCE: 11
gccagttgtt aaggaaccta ttttcta                                    27

<210> SEQ ID NO 12
<211> LENGTH: 29
<212> TYPE: DNA
```

<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 12
aaaggtgtta taaaacagca ttatgattg                                    29

<210> SEQ ID NO 13
<211> LENGTH: 22
<212> TYPE: DNA
<213> ORGANISM: Artificial Sequence
<220> FEATURE:
<223> OTHER INFORMATION: synthetic primer

<400> SEQUENCE: 13
aacatcaggg tcagcattcc at                                           22

<210> SEQ ID NO 14
<211> LENGTH: 24
<212> TYPE: DNA
<213> ORGANISM: Artificial Sequence
<220> FEATURE:
<223> OTHER INFORMATION: synthetic primer

<400> SEQUENCE: 14
cacaatatgg tcagacagct ttcc                                         24

<210> SEQ ID NO 15
<211> LENGTH: 22
<212> TYPE: DNA
<213> ORGANISM: Artificial Sequence
<220> FEATURE:
<223> OTHER INFORMATION: synthetic primer

<400> SEQUENCE: 15
tgcccagtgt ccagttgtaa aa                                           22

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
ccaaaattgg cgttgacagt t                                            21

<210> SEQ ID NO 17
<211> LENGTH: 28
<212> TYPE: DNA
<213> ORGANISM: Artificial Sequence
<220> FEATURE:
<223> OTHER INFORMATION: synthetic primer

<400> SEQUENCE: 17
attcaggaat gacactttt cttttctt                                      28

<210> SEQ ID NO 18
<211> LENGTH: 30
<212> TYPE: DNA
<213> ORGANISM: Artificial Sequence
<220> FEATURE:
<223> OTHER INFORMATION: synthetic primer

<400> SEQUENCE: 18
ataaacagtt ccaaattcaa tttgtacaat                                   30

```
<210> SEQ ID NO 19
<211> LENGTH: 42
<212> TYPE: DNA
<213> ORGANISM: Artificial Sequence
<220> FEATURE:
<223> OTHER INFORMATION: synthetic primer

<400> SEQUENCE: 19
cttagaatag aagtatatct aagtaaaata gtaccaacta cc                          42

<210> SEQ ID NO 20
<211> LENGTH: 37
<212> TYPE: DNA
<213> ORGANISM: Artificial Sequence
<220> FEATURE:
<223> OTHER INFORMATION: synthetic primer

<400> SEQUENCE: 20
caactcttgt tatattatct agtcagatac tctttgt                                37

<210> SEQ ID NO 21
<211> LENGTH: 25
<212> TYPE: DNA
<213> ORGANISM: Artificial Sequence
<220> FEATURE:
<223> OTHER INFORMATION: synthetic primer

<400> SEQUENCE: 21
agcaacaatt cttgacctca aagaa                                             25

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22
gcttggatac ccttccgttg a                                                 21

<210> SEQ ID NO 23
<211> LENGTH: 22
<212> TYPE: DNA
<213> ORGANISM: Artificial Sequence
<220> FEATURE:
<223> OTHER INFORMATION: synthetic primer

<400> SEQUENCE: 23
cagacaagta ggtgggcaac ag                                                22

<210> SEQ ID NO 24
<211> LENGTH: 18
<212> TYPE: DNA
<213> ORGANISM: Artificial Sequence
<220> FEATURE:
<223> OTHER INFORMATION: synthetic primer

<400> SEQUENCE: 24
ttcactcggc gggaacac                                                     18

<210> SEQ ID NO 25
<211> LENGTH: 23
<212> TYPE: DNA
<213> ORGANISM: Artificial Sequence
<220> FEATURE:
```

<223> OTHER INFORMATION: synthetic primer

<400> SEQUENCE: 25
gagttgctca tgctttggct aag                                    23

<210> SEQ ID NO 26
<211> LENGTH: 27
<212> TYPE: DNA
<213> ORGANISM: Artificial Sequence
<220> FEATURE:
<223> OTHER INFORMATION: synthetic primer

<400> SEQUENCE: 26
gcaatgaaat agggagtttg atagaaa                                27

<210> SEQ ID NO 27
<211> LENGTH: 22
<212> TYPE: DNA
<213> ORGANISM: Artificial Sequence
<220> FEATURE:
<223> OTHER INFORMATION: synthetic primer

<400> SEQUENCE: 27
atcatcccaa aaggacgaaa aa                                     22

<210> SEQ ID NO 28
<211> LENGTH: 27
<212> TYPE: DNA
<213> ORGANISM: Artificial Sequence
<220> FEATURE:
<223> OTHER INFORMATION: synthetic primer

<400> SEQUENCE: 28
gttcagttga ttaaacttga tgctgtt                                27

<210> SEQ ID NO 29
<211> LENGTH: 20
<212> TYPE: DNA
<213> ORGANISM: Artificial Sequence
<220> FEATURE:
<223> OTHER INFORMATION: synthetic primer

<400> SEQUENCE: 29
tgatgctgag cttgcaaagg                                        20

<210> SEQ ID NO 30
<211> LENGTH: 27
<212> TYPE: DNA
<213> ORGANISM: Artificial Sequence
<220> FEATURE:
<223> OTHER INFORMATION: synthetic primer

<400> SEQUENCE: 30
agtttcgtaa acaaactgtt gaatgtg                                27

<210> SEQ ID NO 31
<211> LENGTH: 28
<212> TYPE: DNA
<213> ORGANISM: Artificial Sequence
<220> FEATURE:
<223> OTHER INFORMATION: synthetic primer

<400> SEQUENCE: 31
ctttaagaag atcatttagc tcccaagt                               28

<210> SEQ ID NO 32
<211> LENGTH: 22
<212> TYPE: DNA
<213> ORGANISM: Artificial Sequence
<220> FEATURE:
<223> OTHER INFORMATION: synthetic primer

<400> SEQUENCE: 32
cgaaaagcaa tggatgatga aa                                          22

<210> SEQ ID NO 33
<211> LENGTH: 24
<212> TYPE: DNA
<213> ORGANISM: Artificial Sequence
<220> FEATURE:
<223> OTHER INFORMATION: synthetic primer

<400> SEQUENCE: 33
gattcttcaa ctctgccatt ccat                                        24

<210> SEQ ID NO 34
<211> LENGTH: 22
<212> TYPE: DNA
<213> ORGANISM: Artificial Sequence
<220> FEATURE:
<223> OTHER INFORMATION: synthetic primer

<400> SEQUENCE: 34
tgccagaggt ggatggtatc tc                                          22

<210> SEQ ID NO 35
<211> LENGTH: 29
<212> TYPE: DNA
<213> ORGANISM: Artificial Sequence
<220> FEATURE:
<223> OTHER INFORMATION: synthetic primer

<400> SEQUENCE: 35
agctttcaca taattaactt ttctttcca                                   29

<210> SEQ ID NO 36
<211> LENGTH: 27
<212> TYPE: DNA
<213> ORGANISM: Artificial Sequence
<220> FEATURE:
<223> OTHER INFORMATION: synthetic primer

<400> SEQUENCE: 36
ggtcttataa agcatcaaag aggacat                                     27

<210> SEQ ID NO 37
<211> LENGTH: 20
<212> TYPE: DNA
<213> ORGANISM: Artificial Sequence
<220> FEATURE:
<223> OTHER INFORMATION: synthetic primer

<400> SEQUENCE: 37
cccgaccctg atacaatgca                                             20

<210> SEQ ID NO 38
<211> LENGTH: 21
<212> TYPE: DNA
<213> ORGANISM: Artificial Sequence
<220> FEATURE:
<223> OTHER INFORMATION: synthetic primer

<400> SEQUENCE: 38
cgcctgcaag actgaacaat t                          21

<210> SEQ ID NO 39
<211> LENGTH: 27
<212> TYPE: DNA
<213> ORGANISM: Artificial Sequence
<220> FEATURE:
<223> OTHER INFORMATION: synthetic primer

<400> SEQUENCE: 39
ttttacgttc cttttttgtt ttaatcg                    27

<210> SEQ ID NO 40
<211> LENGTH: 22
<212> TYPE: DNA
<213> ORGANISM: Artificial Sequence
<220> FEATURE:
<223> OTHER INFORMATION: synthetic primer

<400> SEQUENCE: 40
cgatcgatcg tttctgctaa ga                         22

<210> SEQ ID NO 41
<211> LENGTH: 25
<212> TYPE: DNA
<213> ORGANISM: Artificial Sequence
<220> FEATURE:
<223> OTHER INFORMATION: synthetic primer

<400> SEQUENCE: 41
tgttcatgtc accactctcc aagta                      25

<210> SEQ ID NO 42
<211> LENGTH: 20
<212> TYPE: DNA
<213> ORGANISM: Artificial Sequence
<220> FEATURE:
<223> OTHER INFORMATION: synthetic primer

<400> SEQUENCE: 42
gcatgcaatc agctctccaa                            20

<210> SEQ ID NO 43
<211> LENGTH: 32
<212> TYPE: DNA
<213> ORGANISM: Artificial Sequence
<220> FEATURE:
<223> OTHER INFORMATION: synthetic primer

<400> SEQUENCE: 43
acgaaatttg aaatcaaata agtagttatg tt              32

<210> SEQ ID NO 44
<211> LENGTH: 30
<212> TYPE: DNA
<213> ORGANISM: Artificial Sequence
<220> FEATURE:
<223> OTHER INFORMATION: synthetic primer

<400> SEQUENCE: 44
acggtcaatc aatttttata gcaattatac                 30

<210> SEQ ID NO 45
<211> LENGTH: 16

```
<212> TYPE: DNA
<213> ORGANISM: Artificial Sequence
<220> FEATURE:
<223> OTHER INFORMATION: synthetic primer

<400> SEQUENCE: 45
gtcgccgcca caaagg                                                       16

<210> SEQ ID NO 46
<211> LENGTH: 24
<212> TYPE: DNA
<213> ORGANISM: Artificial Sequence
<220> FEATURE:
<223> OTHER INFORMATION: synthetic primer

<400> SEQUENCE: 46
acagatgctg ttgagtttga tcca                                              24

<210> SEQ ID NO 47
<211> LENGTH: 504
<212> TYPE: DNA
<213> ORGANISM: Glycine max

<400> SEQUENCE: 47
actctccggc gccgccgccg cgtccaccgc cattggcgcg aaaccgcaga cgccggagtc       60
ctcctcctcc accgacacgc ttccgccgtt cgcctccgac gacaccttgc gaaacgcacc      120
gtttctccac tcggaaacgc ctctcccggg gaaggcgcgc agcaagcgct cacgggcggc      180
gccggggac tggtccacgc gcctgctcca cctggtcgcg acggagcagg agaagctgcc       240
gcagctaaag gcggagccgg cgaagaagag agaaggaacg aatgcggagt gttccggacg      300
caaatgcctg cactgcggta cggagaagac gccgcagtgg agaacgggac cgatgggacc      360
gaagacgctg tgcaacgcgt gtggcgtaag gttcaagtcc gggaggctgg tgccggagta      420
ccgaccggcg gcgagtccaa cgttcatgtc aacgaagcat tcgaattcgc atcggaaggt      480
tttggagctg aggcggcaga agga                                             504

<210> SEQ ID NO 48
<211> LENGTH: 420
<212> TYPE: DNA
<213> ORGANISM: Glycine max

<400> SEQUENCE: 48
aagatccagg ctttccaaca gatagaggga tggattcatc aatatacaac tttgccatcc       60
taatggaatc aacaacgctg tttccccgaa gccgtgcatt gttttgttga actgggaaac      120
cctcatccac aacaacagga ctaatgttcc tgctactgcc acctgtttgc acctcccttt      180
tttgtgccaa attaatatct ttgttggaag agcctgaggg gtaaaatggt ggggatgctg      240
aattcaaatt tgaagcaacc acttgatttt taacaggcac agagccagat tctaccttgg      300
aagcatgtgt ggaagtcctc tccgaactaa caaaacaata cttatcagaa tgtcttgaca      360
ttatatcatg tgcccagcaa atttttaaaaa atgaagccta tacttactgt ttattttgca    420

<210> SEQ ID NO 49
<211> LENGTH: 485
<212> TYPE: DNA
<213> ORGANISM: Glycine max

<400> SEQUENCE: 49
agagaacacc aaggaatctc gttgcactgc attgtgacgg tagtaggaca agcttgatgc       60
```

```
catttgtgag agattcttga gcagtttagg agcaagagca tattaagtaa gaagtgacca      120
gtttgtaaca aaatgttacg taaggacaag gtgatgttta taggcgtagc tgtgatatga      180
tataaaaggg caagtgaggg gtgcatggtg agaagattga tggagtttat atagtgaaaa      240
gagaagttga aataaatgaa ataagggac ttctgacatt ccaaaaacgt tgttgtttca       300
gtgaagtttg aagaaaaagg atgaggttag tggacccaaa aactgtgaat tgatgggatt     360 taaaaaccc ttcttttccc ttgttctagc tttgtctttc tctgatccct tacagcgaga      420
agtcttgatt ataaatcaga taaaaatggc gactgatttg agagaagaaa ggataaagta     480
cagta                                                                485

<210> SEQ ID NO 50
<211> LENGTH: 530
<212> TYPE: DNA
<213> ORGANISM: Glycine max

<400> SEQUENCE: 50
tctggatcat cttttcttgg aaaggatgca acttgggcca cagcgccggg ttgttgtaga     60
aagagaaagg gttttgaagg ctttgaagtt gcatgtgcag ttggagtctt tcaagagctg    120
aagagcttag ggcatttgaa taagaattct cctctattcc attgtttgtg tcttttgcgc    180
ttaagttaga ttgtttgcgc ctcccgagca gtttcttctt caatctagtg ttccaatagt    240
tcttgatgtc gttatctgtc cttccaggta actgagcagc aattatggac cacctataca    300
catagattat atatgttgga acatgtttag ttaatttcta agaatattaa ttaaccaatg    360
aagaagaaga aaacatgtgg agctagctag agagattcta gtgacaaaac aaaaaggaca    420
aacaattatg ttcaaaaact acagcacagg ctcgtagata gagatggggg gttttgagag    480
agaaggacct gcttccaatg ctaatgtaca ggctgcaggc atgcaagctt                530

<210> SEQ ID NO 51
<211> LENGTH: 692
<212> TYPE: DNA
<213> ORGANISM: Glycine max

<400> SEQUENCE: 51
atccaaatct ttggtcctct gtgaaaaaat tcacaaatag cgaagtttcc taatttagat     60
ttagatttat gtatgttata agatagcaat gacaagtaag ggccttcttg tatcatatta    120
ttactgaata atactcatta atagatacta cgcagataat tcaactactc atgttgatgt    180 gaaaatctg tattttaaaa cagtaagtta atgaaaatga taaaaaaaaa agtacttaca     240
ggacggtctg cctcaatgtc atacttcaac acacggaaac attccagcct ttcctccaaa    300
aataaggcat aagtgcgaac ccatgcagaa taatcccatg ctgagcaata aaacaatgaa    360
tgacaactac aaattaaata agcataataa caaaaatgac aataaaatca atcgtggaga    420
gaaagacaga ggcaccattt ggactggaat catcttttaaa atgagccatg ttgagcatat    480
gacttctgct tctcccataa ttgatgagtt cttcatgaaa tgtaggatca acttccctta    540
gagcacggtg aatgacaatt aaagtttttca atgcaaccta gaggtaaaaa acttgtcaat    600
caaccaatat ggaatcaaaa taaaaaccac acatgctcag tggtgattta catgagaagt    660
tgagaactaa agacgactga aggattacat ga                                  692

<210> SEQ ID NO 52
<211> LENGTH: 819
<212> TYPE: DNA
<213> ORGANISM: Glycine max
```

<400> SEQUENCE: 52

```
ttaagagtcg acctgcagac aaagtttgat aggaggaaac tatggtttgc tgaatactag     60
tactttcgtg ccaaatccag actattatag gtactaaaat ttgaatttca tagttgaaca    120
atgaaacata taaataatt aaatatggac tgctatatca aagtttgtgt tcccatgtgt    180
gtgatgtttg cttcattaat tgcttgccag ttgttaagga acctattttc taatagaaca    240
aggagtttta ttaagtgggg tcccatttga actacaatca taatgctgtt ttataacacc    300
tttgtgtggt tatgtacttt cttccttaca gtgcacttct atggcaccga ctcatgggag    360
gccgtgtcct cttaactacc ttctatggga caaagaagat aagaacttat gcacattgtg    420
caaaggaatc cgtaagtaaa attctgtatc tgtatatggt atatgtatta tatgtgaaat    480
ctgatttgat actctcttac agaaagggat cacaatacta gtgctcaact tggacaacag    540
caccactgtt caagtcaatg tggccttaaa atttaacaag ttaccatacc gtagagtggg    600
tgaaccagcc agaagagagt accatttaac tgcaccagac aggaatttac atagccaaac    660
tatgttgcta atggaaaaa tgttaagtgt aaactcagct ggtgaaattc ctcctttaga    720
gcctctatat gtaaactcaa gaaagccaat aatagttggt cctctatcta ttgtatttgc    780
tcatatacca aatgttcttc tttcggcctg caggtcgac                             819
```

<210> SEQ ID NO 53
<211> LENGTH: 1061
<212> TYPE: DNA
<213> ORGANISM: Glycine max

<400> SEQUENCE: 53

```
agcagagtgc aacaaataga aaagggaaaa catccatttc aatagaaaga aaggttgagc     60
tgcaaattgt tgattaccaa tgcaatgggc ttcttccatc attatcagga acatcagggt    120
cagcattcca ttttgaaaca acgtggtaaa ggaaagctgt ctgaccatat tgtgcagcaa    180
catgcgttgt ctgtgtccaa gcaaatcata attagtaaaa ttaacattta cagccacacg    240
cttgtgcttc aagtaaaaca agaatcccaa actaccaaat tagcagatgt aaccagaaat    300
agacagccag gtataagaga tacataacat gctccaaatg ccttaccca gcaatctctt    360
gaataaaggg aaaatgaatc acagcaatct aacctgatat ccattcatat cggcagcact    420
cactcgagca ccctcctgga gtaaaagttc cgcaacctga atagcacccc gaaccgcact    480
ccaatgtaag gctgtctggc cagtatgatc cgttgcattt acatctcccc catgctgcca    540
accacaaatc aaccagttaa tttaggataa gactaattcc atacttaata tcaagccaaa    600
tttggctaca tacattcaat tgcaaaacaa acaaacacca cattcgattt ccatttccat    660
aacacaaaca tgacctacaa gccaacctga gctgagctga gctgagctga gctgagctaa    720
gctactttaa caaattcaaa ccaccaaaaa catcataatc aaatgttctt ctcttctaca    780
tctatatcat tccttcctta aacagcaata agtaactaat tcttcatttt tcttttcttg    840
gagtaaaaaa atagtaattc agcgagtgcc aaaataacat acgcattcaa acaagcacaa    900
taaaagcaaa gtaagcaaag caaacacaat tcaacaaacc gatcaaagaa cctcaatgat    960
gtactgagca gcggcagtgc gattgttgag agcagcccac tgaagcgcgt agtatcccaa   1020
cccgtcgggc tcggtgacgg ggcaaccctc ttgctccacc a                       1061
```

<210> SEQ ID NO 54
<211> LENGTH: 961
<212> TYPE: DNA

<213> ORGANISM: Glycine max

<400> SEQUENCE: 54

```
ctgtttttca gtgcccagtg tccagttgta aaaaagcttt taaggcggtg tttcaactgt    60
caacgccaat tttgggatta tatgctttaa ttattacaag cccgttgatt atttattacg   120
accgacatga tacgtaattt aagaaattaa actaatgtat tagtctcggt acattgaaaa   180
gtacacccat tggccaccca gtaatttcct cacaattgct caattaaaat taaaagtgga   240
cgcttaactc tgtgcccttt attaaaattt gcaaatctta atagagaaaa acataagcta   300
aaacttttgg tagtgataat atgaagaaaa aaatcactgt tattaatcat aaatttaaca   360
taaaaaacct attatcatat aaagggaatt tgaacctaaa gggaattttt tcttcctttt   420
actcaagcgc cttgtgtacc atcttaaaca tacaaatgat tactaatttc atagatcaaa   480
tttcgctcct ctttatgatt gattgaagct gtgttcaatt tggaggtggt taacgtttaa   540
ttttctaggt tgttggttga taatgtagac attccaagtt caatcgtgtt gaagcatttt   600
aaattaggct ttgttggctt gaaaagtaaa aacggctgct accattttc ttcctttgcg    660
ggtgctaatt aagaagtcaa caaagtgaac aaaccatgtg ttttttcaata ccaaatgttg   720
taattttgc caagcataat cttcttccgt gtgctagctc acattacaag aagaagatag    780
atttgaataa acacctcagg ttaagttgag tcaaattaat tgcagttagt taattttttt    840
gccaaactca gtcctttacg ggccatggat caatgggccg ccccacaagt tttttttta    900
aaaaaaaat gtttaatcac atcaacaaca tgatctttaa ttagaagtta tgacttttc     960
t                                                                   961
```

<210> SEQ ID NO 55
<211> LENGTH: 574
<212> TYPE: DNA
<213> ORGANISM: Glycine max

<400> SEQUENCE: 55

```
cactgtgcca aaaatgtcgc tggcgagcga ctagatgatg gtttcttgtg agtatcttta    60
gtgcttcgac attaattcag gaatgacact ttttctttc ttagtttcat tttaatttct    120
aataagatat gagtgagata ttgtacaaat tgaatttgga actgtttatt atatttaatc   180
aggttctagg aatgtttaga ggaaacttcc gatgttattt aatgtatatt tttgtatttt   240
tgtttctcag atgttgtgga agctgtggga gggtgttgga agattacttt tttgccgagg   300
agccttcatt tgttaagaat gcagcggggc aggtaatgga agcttgacaa gctaaggtgg   360
ttttctggga gattgaaact ttatttctt tttcttaaat taacaacatc atgtcacggg    420
agaaagaggc ttgagctact tctatgaagg actgatgggg atttggatta cttgaggttt   480
aagtttgatt gtgggtatgg tttgagagag aaaggaagaa tacatggatc ccaccatgag   540
gtcctatatt tgagacctgc atggtatctt ttct                                574
```

<210> SEQ ID NO 56
<211> LENGTH: 1206
<212> TYPE: DNA
<213> ORGANISM: Glycine max

<400> SEQUENCE: 56

```
atttgatcca atgagaaaaa ttgattgtag tatatgccct acagcaaatt ttcaacaacc    60
agattaaaga acaaaaaagc acattctaag gataaacaaa acagaaaatc catacccata   120
tatttgacaa cctgtaaaca aaaaaaggag taaagcatac tttgttttta tcattttatg   180
```

```
tttagaccaa agttgccaaa ctaaactcaa attcactatg tttacctact tttttcagta      240
gatcgctagc aaaaaataca tacattaata ttggtagcaa caaatcatta taaataacat      300
cataaagtgg aacaaaataa accaaaaaga tagttgacca gaatatatat ctaaaccatt      360
tagtttgggt tctgggctga atggtgacac ttagaataga agtatatcta agtaaaatag      420
taccaactac ccaggaaatc agataacagc aagatactaa gttacagaca aagagtatct      480
gactagataa tataacaaga gttgaactat gatacatgta acagaaacaa caaattatca      540
attgctaaaa ttaacaatta cctttatgtg atacaatttc aatgctacag tcaaagccac      600
catggtttcg atcacaagag cagaagctga ggccaaaaag taaacattaa aaatggtaaa      660
tttctttagg aagttgtgtg ccacaaatac aaatcaagca atctggaatg tctgtaactt      720
agtatctgac tattttacaa aaatggctta gtcaatacca aagattcaca tggttcttat      780
ctactaatat aaaacaaaca aatgaaatgt aaacagaaca gataaattga gaacaagaaa      840
agggtttaac ataaacctgt atgatgtcaa tccactggca tcaaaagaat atttacaatc      900
tccatgagag gagcattgtt tagggcatcc ttcaagtgaa atagacatga cagtttgtgc      960
tttcaaagaa tcactgccgg tataaagatg tcttagacct ataccccaag ttccttctct     1020
agcataaata atgtaaaagt caattttgtc atcacttgaa tcatatagca tgaaaaacac     1080
agattgatca ctcttccttg tcatgttagc ataataatag tcccagctat caagagaagg     1140
caatccacca aatctagcat agacttcata acgtatcttc acatctgcag gcatggcaag     1200
tctggc                                                               1206

<210> SEQ ID NO 57
<211> LENGTH: 1562
<212> TYPE: DNA
<213> ORGANISM: Glycine max
<220> FEATURE:
<221> NAME/KEY: unsure
<222> LOCATION: (1)..(1562)
<223> OTHER INFORMATION: unsure at all n locations

<400> SEQUENCE: 57
tactttccag ctgatatgct caccatattc cttccacaca tagcatacaa ctgttaaaaa       60
aaaataaaca aaaaggggggg aagtgttttt aatcaacatg ttttgtctcg ggaaaaataa      120
aatacatgtg aagagaaaaa ttcagagcat aataagaacc tgttggcatc taagatcagg      180
atcagaagag acccaataaa ataatgcacc atcatctgta agagccatgc tgtgtaccat      240
tccagcagct atagaaacca cattaagtcg ttccttgcgg tgaaatttta aaggagtgct      300
tccacttttc tttaagtttc tactaactac tacacgtttt ggagtaacaa gtcgatgacc      360
ccaggtaaat acctgcaaaa tatggaaaat ttgaacttaa agatgaaaac tagaaagtac      420
ttttatttcc aaaaaaaaat ggaaaataaa gtactaacaa gttgaagacc ccaggtatat      480
gctcgtgata aaactaataa tggaaaaaat gctatgtttc atatccatgt accttaaaaa      540
ataaagcagt tgaacttgaa cataatttta ggaaagaaca ataatactat aatagaactc      600
aaacttaggt cttatccccc tctgtaaaat gtatatattc caaaactatg taatacagga      660
gcagtagaaa agaaaataat taaaattgca gttagctttt ataatttcaa gatattttaa      720
ttcattntgt gggcttcagt ttatgagtaa aattttagtc cagatttatg catagtgttt      780
taggtggtgc cttatttgca aggcccaagg aattttcat gccccttggg ttagccttta       840
actgaggctc aaatatgaag atggtaacta gagtttctta aaattaaaag aacttgaact      900
```

```
tttaacaaaa tgacaataat ctgcaattag ttacctctcc gtcagatcct aatacaattg    960
tgtgatattt tgcagcagaa actctggtca aagtcttccc cttcaaggat tcaaccacat   1020
gtggggtgta attagatgct gagtttgagg tgccataacc aagctgaccc tccctgttgc   1080
aaccccaagt aaaaacttcg cccaaatcag aaactacagc agtgtgtttg tttgcggcag   1140
caacagcaac aattcttgac ctcaaagaag atactctacg aggtgtgggt tgtgtatcaa   1200
cggaagggta tccaagctgt ccctctgcac aacaatgaaa caagaaaata gacatgccaa   1260
ttatgtgtca ttctcatttt tcaaaaaatg cagaataaag cataaagaaa actaattct    1320 ttctcaatta atcagtgatg attggtagaa actagaaaac cataagtata cttgataaaa   1380
caaaaagtag ggaagggatg caggggaaaa gattatttga ttgcaattta gttaagtagt   1440
ttacagtaac aactcacaag actcacaact tatacaaaca tgaatatcgt caagttttac   1500
ctctattgga tccccaggtg aacacttccc caccctgggt agaaataacc gtatgatgct   1560
ta                                                                  1562
```

<210> SEQ ID NO 58
<211> LENGTH: 1099
<212> TYPE: DNA
<213> ORGANISM: Glycine max

<400> SEQUENCE: 58

```
attgctttt accactgcac ttgatttgct gtaggataga ttttcttggc ttcactatga     60
taaaatggag ggtttgcatg ctggataaca ttttaggag aggaaatcat tcatgggcat    120
ccatcgaata gcttaagctt cataggaaag gagagtttag gaatatgatc cttgtcaacc   180
cccattttac atattgaagt caattttttc cacaaatgga cctgcacata attcatgatt   240
cttgcccaaa gatcttttgt gtgtgagggt gtgttagaca tgtccaaacc attctttgtc   300
ctagcagtta caatggaaat ttgaggagtt ctgatagtaa tatagtatag ttgaaggctt   360
ttttatatct cagaggtctg ccctttttt tttttgatc agcaaaaata tgatatgtta     420
taaatagatg aaagtaccag gggtactaaa gatacaatgt taattctagg taggctgctg   480
gatccaattg tgttaggatc caagctgcag caaagaccac aattcacaac aatctaagag   540
acaaccgcgc acacaaatta agatatcttt ttttcacagc tacatacgaa cattcatccg   600
cacaatgcat aaaaaaacaa aagcttcaaa cagaaaagca agaaaacacc aaaaacacat   660
tcccaataac ctagtaaaca gcaaaagaac cacagcaagc aaaggtacct tcgaacaacc   720
ctctgcaatt tgggcaagcg caatgagggc agcatggtgc ttctcccact caggagcaga   780
caagtaggtg ggcaacagct cagaggcaac tggcacaatg gtgttcccgc cgagtgaaat   840
cgagagccta tccaagcact cctgcccaaa gccatagtta ctcgtctcgc ccgcgtcctc   900
ttcctcatcc tctgcaccgt gccacgcagg atcatcctcg atatcaagca acaaattcat   960
caacacacca aaaagctttc tcacaaactg tggcagcttc ctcatcattc caggagcacg  1020
ctccctcgcc tcagcgagag taacgacaaa ttcaatcgcc aagtgccgtg ttccttcctc  1080
caaggcctcg gcctctgcc                                                1099
```

<210> SEQ ID NO 59
<211> LENGTH: 264
<212> TYPE: DNA
<213> ORGANISM: Glycine max
<220> FEATURE:
<221> NAME/KEY: unsure
<222> LOCATION: (1)..(264)
<223> OTHER INFORMATION: unsure at all n locations

<400> SEQUENCE: 59

```
nggctgtcaa gtttgcgata tcattattgg gattgcaaaa tgtggatttt gaaacagata    60
acaaagaagt ggcagataag aggcttttgt ctttgaatcc aacttatgct gttggttttt   120
tgaggagaca tagtatggag ttgctcatgc tttggctaag acatctctat ccttcactag   180
tcttcaagtt ttctatcaaa ctccctattt cattgctcat ttaattaata atgaaatgcc   240
ttgaatttgc tttcgtcaag gaaa                                          264
```

<210> SEQ ID NO 60
<211> LENGTH: 1014
<212> TYPE: DNA
<213> ORGANISM: Glycine max

<400> SEQUENCE: 60

```
atttcaaaca gaaggggatg agtacagcaa gcacatctta taatattcca ttttttaagc    60
atctgcttca ctacttttg accttttgc aaactttaat acaatccaat taagattgaa   120
aacgttcctt tgactaccaa accaggcaac tcaatttaac gattaccaaa gatttgtaag   180
ttggtctgaa agtagcagac aaaaaactaa ttaccaatac gtaagcaagt atttgtttgg   240
cacaaatatt gttaataatt tatgtggtat gtgaatattt agttgcaagg catacatagc   300
caactaatct ctgaacgaag aaaaatgaca aatcttggag actgaagcac atgaattgaa   360
ttgagggatt atatgaagtt tggaggagca cctgttcatc attgatcaat ggcgtgatca   420
atcaacttta ggcctagcag cttgaagcat ctcaacaatg agagtcttca catccctaaa   480
agaaaaacag taaagaatc acttctctgt ggaaaataaa cccaacatgc ttcaggaaag   540
gttattcttc ctaattcctt atcggaaacc cataagccca tggcaatagg aagctcacaa   600
cttagttatt cagcaaagga gtccttggca tggacatgat gaatctcatc atcccaaaag   660
gacgaaaaaa gatagaaaag tggtatttgt ttgattaaca gcatcaagtt taatcaactg   720
aacagtaaag cctagactaa tacagtaata ctaccatttt catcaaattt cacacaagca   780
tggaattgca taagtaaact ggaaaacaga gagcatatt tgatctaatg aatatagata   840
tgtccttttt tgcagatggg agtttatatc aaatatgatg tctcactttc tatcttcagc   900
acgtcgaggg aaaggtacac gaagcttgaa agtatcaccc tggtaaccag cctacaaaaa   960
aaaaaatctt ctaataaata aggtgcaaat ttcaaactca aaaaactatc caaa        1014
```

<210> SEQ ID NO 61
<211> LENGTH: 1505
<212> TYPE: DNA
<213> ORGANISM: Glycine max

<400> SEQUENCE: 61

```
gcctagactt ggctgcctgc agctgctcta gcttctgatg ctgagcttgc aaaggcatag    60
aatgtcctat gatgacacat tcaacagttt gtttacgaaa cttagaaagc cagtgaatag   120
ggacaccata aataaacagg aggattgcag aagttgcttg agtggaactc gagcttggtt   180
ggataatata ttctttttaaa gttcagacat cgtgtttcca ttttttcttaa atttgagtat   240
tttgaatttt taggaggatg gttttgctcg catcctcctc ttgctgaaaa ctttgtaggt   300
aggaatgata taattttgca tgctaggttc tctacatgcc attgtcaaac gggaatactc   360
atttgtttc ttgtctgtgc ataagcacag acgcatttgc aaatgtctag attgagataa   420
ttttactcc ctttatttga ttatttcttt tggaaaatgt tccttttttg ttgtattgca   480
```

```
atcatcagct ctcttaaacg actgttatca tgagtcaact actagctatt taatcccttt      540
tttgttgtga ttagttccgg ggaaaatgca aagattgttg ctaggtgcac ccagcattat      600
tgctggtgca cccaacattc tttaaaaatg acaaaattgt ctctgctaat ttcttcccctt    660
acgaatcaag ttgattcata agttgatttt taagacttac ggatcaactt aatccgtaaa     720
aagacttaca gatcaagttg attcgtaaaa gacttacgga tcaagttgat tcgtaaaaga    780
ctacgggatc aagttgattc gtaaaagact tatggatcaa gtcttgatcc ataagtctta    840
aatattaact tacgggatca acttgatccg taaagtgtat ttttgtcttt tcgtggttag    900
tgctgggtgc atcagcaata atgctgggtg cacctaggca gcactcaaat acaaaattga    960
tgggaatcca gtcacctatc gcgatcgata tgttggactt ctcgttatgg gtcttaatga    1020
ttttgaactg aatgcatata tatcaagatt gcacactaaa agccacgagg cagctcaaag    1080
gtctactact gtaatgagta agcttgaagt gaagagcttt tgaaagttct ctacgaaaag    1140
tactaaaacg ttagaataat ttattaataa aatatacgag gatagttaat caagaaacct    1200
gctataacta acagtagtga gtgggtatag atagatgaaa actattggta aacatcaaaa    1260
cagaacaaaa aattgaccte ttgattaaga tgtattttt agaatatatg tatataataa     1320
acaaataatt aaaaataatt acatatgata tcacaaaaaa aaaatgtcaa tcttataata    1380
ttcaaataat ttaaccgaaa aaagtacccc agaaaaacat ctttaaatat tgattaattg    1440
agaagtacaa caataaacaa ccttattgca tccaagtaac agtttattat tacactctgc    1500
gcaaa                                                                1505

<210> SEQ ID NO 62
<211> LENGTH: 1088
<212> TYPE: DNA
<213> ORGANISM: Glycine max

<400> SEQUENCE: 62 aattttttg tataatcgac cccatattct tgcttgtatc ccttggcccc aagcgcgcct       60
tatacttgtc aacttcacca ttttctttaa gctttgtttt gaagacccac tttacgccaa     120
tggttttgtg tcctttaaga agatcattta gctcccaagt atcatttctt ttaatggcat     180
caatttcatc atccattgct tttcgccatt tttcttcttt gacagcacta tccaatgttg     240
tagggtcaca atctgaaaat aaggcaaagt gaatagtagg atcttcagtt tggtcaatcc    300
cagttacctt ataatttgac atccatgctg gcctcgaaga cgtttagatt gagttgcagc    360
tgttgcgtct gttgttccag catttattgg tgttgaaatc tctgtttcaa gagctatttg    420
agctgcattt ggagatgtta agacagtgtt tacagctgca attcttttac atcttcattg    480
tcaacaataa ttgaattggg ttgctgctca ttccagtccc atgtgttgtc ttcatcaaaa    540
ataacatccc tgctggtcac aatcttcttt gttagtggat taaataactt atatgctttt   600
gatgtttcac ttcaccaac aaagacacac ttttcagctt tgtcaacaag cttcttcctc     660
ttctcatccg ggatatgagc ataggcaatg cacccaaaat ttttgaaagg atccacagat   720
ggttgtctcc tactccaagc ctcttccggt gtcatgtttt gaacagaaaa agttgggctt    780
ctattgagca catgaatgct ccaattaact gcttttggtc aaaaagtttt cggtaatctt   840
cctcttgtta acaaacttct taccatgtta aggataattc tattttccct ctctgataca    900
ccgttttgtt gtggtgtata tgctgctgta agctctcttt gaatgccatg atgttcacaa    960
tacgcttcaa attcttttga gcaatattca ccaccacgat cagttcgaag agtctgaatg   1020
gtctttcttg cttcattttc tacacgagct ttgaagcttt tgaaagtaga gaaaacttct   1080
```

```
gatttgtt                                                                    1088
```

<210> SEQ ID NO 63
<211> LENGTH: 900
<212> TYPE: DNA
<213> ORGANISM: Glycine max

<400> SEQUENCE: 63

```
catagaatgc taaggaagct aacgaagtt ggttgcagac ctgaatgaac catctgttca    60
aatgatctaa gagcatggcc accgtctccg ttttgtgcat aagctgaaat cagtgcattc   120
caggagactg agttcttcac aggcatctct tgaaacattt gaagtgcatc ttttatggat   180
ccacattttg catacatgtc aaccagtgca ctcccagaaa atacatttga aatgcatcct   240
gatctgatta tatgtgagtg taactgtttt cctagtgtca gtgaagctag atttgcacag   300
gctcttaaaa tgctggcata agtggccgag tcagcaccta ttttggctct tgcatctca    360
acgaatagct ttaggccatc ttcatggagt cccttctgaa cataacccga gatcaaggct   420
gtccatggaa ctgaactttg atgtgccaga tctgcaaaaa tcctatttgc ttccccaaat   480
ttgtcacatt tagcgtacat gtcaactaac gaattcctaa ccagaatttc tgaaatggct   540
tctgttacaa tagcctggga atggatttgc ctacccattt ccagattcaa agcatttgca   600
gcaatgctca acaaggtagc aaaagggaac tgcctccggt caaatctagt aaactgtaac   660
tccctgaaaa gttcaagaga ttcttcaact ctgccattcc atgcacaaca catgatgagc   720
acattgtaag agataccatc cacctctggc atctcatcaa aaagcttcct tgcctcaaca   780
atccgatcat gcttcgagta gaaatcaagc aaagaattag ccacaaacac attccacaca   840
aaattacact tcaccacaaa actgtgaact tgttgcccaa actctatatc atccaactgt   900
```

<210> SEQ ID NO 64
<211> LENGTH: 1252
<212> TYPE: DNA
<213> ORGANISM: Glycine max

<400> SEQUENCE: 64

```
ggccagcttg catgcctgca ggagaagtat cgcaaaactt aagagtgaag gaaaaagcag    60
tgttgttcag ttttcacct tctcttattt taagcctagc tttcacataa ttaacttttc   120
tttccaaaac tcaagtttat gatttgaaaa actatgtcct ctttgatgct ttataagacc   180
atatagattt tcttgcctag aacagtggtc ataatttgg aactatagtg actttgctgc   240
tgtataaatt tatatttaat atagaattat caattttctt attgcatctc aaatctcaat   300
gcctacctat tcctcctcat gcaggacatg aagcggcaat gtgatgaaaa aaggtttgta   360
tttacacaac tgctattgtt ttttctcatc attatgtgat gtttcctgaa tctgttttat   420
tgccttcaga gatgtttatg aatacatgat tgcccaacag aaagagaaag gaaagtcaaa   480
aagtgctaaa ggtgaaagtt tcacgctaca gcagttgcaa gcagctcatg ctgaatatga   540
agacgaagca aaactttgtg cctttcggtt aaaatcgctg aagcaaggcc agtcacgcag   600
tctcctaaca caagcagcgc gtcaccatgc tgctcaggtt tcttgaact atgaccttc    660
tcattcaaat cttttatcat ttcttcagcc tagtcttgat gcatctttgt tcttgttctt   720
ctttcaatat agttgaattt cttccggaaa ggacttaaat cactagaggc tgttgaccca   780
catgttagga tgattgctga acgacaacat attgattacc aattcagtgg cctggaggat   840
gatggaggtg aaaatgataa taatgatgat gggaatgatt ttgacgtcat tgaaggtggt   900
```

```
gagttgagtt ttgactacag ggcaaataag caagggccat atattgtttc cacatcaccg    960
aactcagcag aggtaggaaa tttgtattac tcaaaacttg aatggttttc aaagcctggg   1020
tgcatattga actttattct tattgctcat ttgctttttt atttaaaata ttaccaaact   1080
ttgtcacagt tgtcatttta tacttgttgc agtctatagc tcgctacaaa ttaaaaacat   1140
tccattgttg ttttcataat ctgaactata aattcatctt atcataatca ttggcaatgt   1200
tttgccaggt ggaagaatca ggccgttcat atattcgagc ttcaacccca ga           1252

<210> SEQ ID NO 65
<211> LENGTH: 439
<212> TYPE: DNA
<213> ORGANISM: Glycine max
<220> FEATURE:
<221> NAME/KEY: unsure
<222> LOCATION: (1)..(439)
<223> OTHER INFORMATION: unsure at all n locations

<400> SEQUENCE: 65
cagccgtcac agaaaaaggg ctggttgcaa tatcaatggg ttgccctaag cttcactcat     60
tgctctattt ctgccaccag atgacaaatg ctgcactcat aacggtggct aagaactgcc    120
cgaattttat ccgattcagg ctgtgtatcc ttgatgcaac aaaacccgac cctgatacaa    180
tgcagccact ggatgaaggt tttggcgcaa ttgttcagtc ttgcaggcga ctcaggcgcc    240
tatccctctc ggggcaattg accgaccagg ttttccttta catагgаatg tacgctgaga    300 agcttgaaat gctgtccatt gcatttgctg gggagagcga caaggaatg ctctatgtgt     360 tgaatggatg caagaagctt aggaagcttg agattagaga ctgccacann nnnnnnnnn    420 cnnnnnnnnn ngnngnggg                                                 439

<210> SEQ ID NO 66
<211> LENGTH: 575
<212> TYPE: DNA
<213> ORGANISM: Glycine max

<400> SEQUENCE: 66
accttcttcc ttcaaatcaa aacaatttaa aaaaacccctt cttttttttcg aattaaaata    60 aaatgttacg atcctcgtaa gctttcagca tgacacgtaa ttgggtttgt ttgtttgatt   120
gttttgtgaa acataaggaa gccgaaggcg tcagtgaatc gaccccccac accagatgtg   180
gccgaaaatg ccccctgaaag ggaacccacg cttcaagagc tcatcaacat caaggtttca  240
tcttttcttc ttttttcttct ttttttttcag ttttgagtta cttctttgtt ggagtggtta   300
tgggtcttga aaggtaaagt ttttttacgtt ccttttttgt tttaatcggc aaatgttaat   360
tgttagttta tttagttttt ttcttagcag aaacgatcga tcgaacccgt gacctttttc    420
ttcttccatt ttttattaac catgcaacca accttatatc tctgtgttgt tgatgttgtt    480
gttcagttga tcgagaccgg agagaaggag cgtctcatgg agctgttgag ggaaaggctt   540
gttgattgcg gttggaagga tgaaatgaaa actct                               575

<210> SEQ ID NO 67
<211> LENGTH: 597
<212> TYPE: DNA
<213> ORGANISM: Glycine max

<400> SEQUENCE: 67 gttttttcctc actctctcca tcatgttcat gtcaccactc tccaagtagt tactcccttg    60
caagtcatgc taacttggag agctgattgc atgcttctct gtaacataat cctagtgtac   120
```

```
accttaatag gatgggtttc aattattcag ttgttgaaaa gtcattacta ctcagctagg      180
aaaggcaggc atggaatggc cattttctaa ataatttgtt ataacaattg aagagagtga      240
taacagggta agaagtgagt gaaagctaca gcctacacaa agagagaac ttactttgaa       300 aggaatttat aaaattgaat caccaaatcc aggtcattct catataccgt actgagtttt      360
cccaggcatg agatgccaaa tcttgggtct gttgtataaa ttatattaat aacaatgttt      420
cagaataaaa tactatgaag tttggttata caaatacaat agaacagatt ctgcatgcaa      480
ccattccatg tatcaaaatg ctcaagttaa ccccacagct atcctagact atataatggg      540
aggaaaagaa atgtaaagta aaataaaagt taagaaaggt cattcctttc aaatgta        597

<210> SEQ ID NO 68
<211> LENGTH: 2011
<212> TYPE: DNA
<213> ORGANISM: Glycine max

<400> SEQUENCE: 68
tagagtcgac ctgcagcgac gaatattgat accttcgaga tcgtcgccgt caagatcgta       60
tgctgctttc tgttcctacg cttttttaat tcaattagtg cagtttcagc ttcgtttgat      120
ttattttttt tatcagcaaa ggtaagctat atattaattg gagtaccaga ggtactgaat      180
agtacataaa ggaccataca aatggttcca caatcagaca ttcatattct gaaagggaac      240
cagagtatgg atatagattt gttctgaaat ttacattaaa taggctcata acgatgtagt      300
ctactactga tactaaaagc tttgtgtaaa gctgcttgcc cattgattga aatggactgt      360
gaaacctttc tcaaaacccc ttagccaaga ccacagtagg aaagtcgcat cttcaaacag      420
tgcattagca ttgaaagtgg cattagagaa cactatgttg tttctaagct tccaaatgga      480
tcatgttaag gctaaccacc agtattgcca tctgttcatc cttactccat caagttgaac      540
acccaaatgt tgtaggaaat gctgcttttgg gcttaatggg aaagcacctt taatgtgcag      600
ccatgtcata gtgtcccacc aaatgggttt tatgttgctg caatgtagga ataaatggga      660
tgcatcttcc tcttgagatc tgcagggttt gctatagtaa tgaaattgta caaagcacca      720
aagtttctca aaccaaacaa ctctgaggct gtagctggaa caattgccca atgagctcca      780
taaccaagtc caactagtaa cgtgccaaca tacattgacc ctggccatcc cataccaagg      840
aaaacatgcc caagagtcat aatgagttga atacagccca atgcaactgg ccttggatat      900
gcatgatccc tgctcaagaa aaaaacacaa cgaaatttga atcaaataa gtagttatgt       960 tagatacatc gtacacctaa atatttatat cacgtttgtc atgtatgata agattattaa     1020
cttttgtata attgctataa aaattgattg accgtgtaaa aagcataata agctgaatta     1080
aacatgcaat caatgtataa actgattttt tttacctcac aacaagctca gatatgtaac     1140
ctcctccgac acggccaagg aagttccaaa tactgatcat ggaaacaaat atatgtgcat     1200
tgtcgaatcc tagagactgg ctcatctgac ccagattgtc gattacagtc aatccggatc     1260
cagaacccat gatcatggaa atgaaaagaa gccaaaagtc tgctttgatc aatgcttgtg     1320
tcaaggtgaa atcttcccct ctgtgtggtc ctctccttct cttaaccctc actgctcctt     1380
ctgcaggtag taaacatcca tccttaaaaa agttgcatag ccctcgtgat agtgatcata     1440
acggtttctt gttgaatgta gaaaaacaag aggctccaaa agccagagtt aagcgtagcc     1500
tttctgaaaa catgccggtc attagtagat tcaaaagttt ccgtcaaata tctcacagga     1560
cttcatcatt gaaaataaat ttgatccgta gtgattctgc tcaagattgt gtatgtcatg     1620
```

| | |
|---|---|
| attcttctct tacattatcc aatgcgttgg atggagatca atctgaggca tcgggtgaaa | 1680 |
| gtactttggt ttatgaaagg gaatatgtac aaggagttct aattatggag agaatttgtg | 1740 |
| agtgctctga gtcatcacgt gaaaagaaac agcaaaataa gtttagtgtg aagcaagtaa | 1800 |
| agaagagttc atgtttggac attttttgaag gccggcgaag ctattatctt aagcttaatt | 1860 |
| tgcagcttgg catcaggtaa aataatttac taaatgttta cagtgacccc ttctaaatta | 1920 |
| tttttggaaa aattgatagt tatgttaaca ttaatagttg tcgatattac catactttca | 1980 |
| agtaccttat tgttttggaa tcatggccac t | 2011 |

<210> SEQ ID NO 69
<211> LENGTH: 379
<212> TYPE: DNA
<213> ORGANISM: Glycine max

<400> SEQUENCE: 69

| | |
|---|---|
| cttctgactc caccccttca tctatcagtt ttggtcgccg ccacaaaggc ttgtcatttg | 60 |
| tccctcgagc ggttcagcgt ggaggtggat caaactcaac agcatctgtg acaaagaaat | 120 |
| aagcttggac tcaaacaaat ctgcattctt aattgctgaa taatcaacat gcagatgcag | 180 |
| ctccattata aaatccgtgt ggacgtcttg cattctaagt ttgaagaagc caattaagtt | 240 |
| gaagatggaa aattagaatc atgctggagg atgtaataac agcatttgtc attattatct | 300 |
| ttttttgctc ccacttgggg ctgtaagttt gcccaacaca ggcaatatga gcatgcgaat | 360 |
| atgcctggct tgtataatg | 379 |

<210> SEQ ID NO 70
<211> LENGTH: 16
<212> TYPE: DNA
<213> ORGANISM: Artificial Sequence
<220> FEATURE:
<223> OTHER INFORMATION: synthetic probe

<400> SEQUENCE: 70

| | |
|---|---|
| aaccttacgc cacacg | 16 |

<210> SEQ ID NO 71
<211> LENGTH: 13
<212> TYPE: DNA
<213> ORGANISM: Artificial Sequence
<220> FEATURE:
<223> OTHER INFORMATION: synthetic probe

<400> SEQUENCE: 71

| | |
|---|---|
| tacgccgcac gcg | 13 |

<210> SEQ ID NO 72
<211> LENGTH: 14
<212> TYPE: DNA
<213> ORGANISM: Artificial Sequence
<220> FEATURE:
<223> OTHER INFORMATION: synthetic probe

<400> SEQUENCE: 72

| | |
|---|---|
| caacgttgtt tccc | 14 |

<210> SEQ ID NO 73
<211> LENGTH: 13
<212> TYPE: DNA
<213> ORGANISM: Artificial Sequence
<220> FEATURE:
<223> OTHER INFORMATION: synthetic probe

```
<400> SEQUENCE: 73
caacgctgtt tcc                                                        13

<210> SEQ ID NO 74
<211> LENGTH: 18
<212> TYPE: DNA
<213> ORGANISM: Artificial Sequence
<220> FEATURE:
<223> OTHER INFORMATION: synthetic probe

<400> SEQUENCE: 74
atcaagcatg tcctacta                                                   18

<210> SEQ ID NO 75
<211> LENGTH: 18
<212> TYPE: DNA
<213> ORGANISM: Artificial Sequence
<220> FEATURE:
<223> OTHER INFORMATION: synthetic probe

<400> SEQUENCE: 75
tcaagcttgt cctactac                                                   18

<210> SEQ ID NO 76
<211> LENGTH: 13
<212> TYPE: DNA
<213> ORGANISM: Artificial Sequence
<220> FEATURE:
<223> OTHER INFORMATION: synthetic probe

<400> SEQUENCE: 76
acagcgccgg gtt                                                        13

<210> SEQ ID NO 77
<211> LENGTH: 13
<212> TYPE: DNA
<213> ORGANISM: Artificial Sequence
<220> FEATURE:
<223> OTHER INFORMATION: synthetic probe

<400> SEQUENCE: 77
agcgcagggt tgt                                                        13

<210> SEQ ID NO 78
<211> LENGTH: 14
<212> TYPE: DNA
<213> ORGANISM: Artificial Sequence
<220> FEATURE:
<223> OTHER INFORMATION: synthetic probe

<400> SEQUENCE: 78
acttctgctt ctcc                                                       14

<210> SEQ ID NO 79
<211> LENGTH: 16
<212> TYPE: DNA
<213> ORGANISM: Artificial Sequence
<220> FEATURE:
<223> OTHER INFORMATION: synthetic probe

<400> SEQUENCE: 79
tgacttctac ttctcc                                                     16

<210> SEQ ID NO 80
```

```
<211> LENGTH: 15
<212> TYPE: DNA
<213> ORGANISM: Artificial Sequence
<220> FEATURE:
<223> OTHER INFORMATION: synthetic probe

<400> SEQUENCE: 80
atgggacccc actta                                                        15

<210> SEQ ID NO 81
<211> LENGTH: 15
<212> TYPE: DNA
<213> ORGANISM: Artificial Sequence
<220> FEATURE:
<223> OTHER INFORMATION: synthetic probe

<400> SEQUENCE: 81
tgggatccca cttaa                                                        15

<210> SEQ ID NO 82
<211> LENGTH: 16
<212> TYPE: DNA
<213> ORGANISM: Artificial Sequence
<220> FEATURE:
<223> OTHER INFORMATION: synthetic probe

<400> SEQUENCE: 82
tttaccacat tgtttc                                                       16

<210> SEQ ID NO 83
<211> LENGTH: 17
<212> TYPE: DNA
<213> ORGANISM: Artificial Sequence
<220> FEATURE:
<223> OTHER INFORMATION: synthetic probe

<400> SEQUENCE: 83
taccacgttg tttcaaa                                                      17

<210> SEQ ID NO 84
<211> LENGTH: 15
<212> TYPE: DNA
<213> ORGANISM: Artificial Sequence
<220> FEATURE:
<223> OTHER INFORMATION: synthetic probe

<400> SEQUENCE: 84
ttaaggcggt gtttc                                                        15

<210> SEQ ID NO 85
<211> LENGTH: 13
<212> TYPE: DNA
<213> ORGANISM: Artificial Sequence
<220> FEATURE:
<223> OTHER INFORMATION: synthetic probe

<400> SEQUENCE: 85
aaggcggcgt ttc                                                          13

<210> SEQ ID NO 86
<211> LENGTH: 21
<212> TYPE: DNA
<213> ORGANISM: Artificial Sequence
<220> FEATURE:
<223> OTHER INFORMATION: synthetic probe

<400> SEQUENCE: 86
```
ctcactcata tcttattaga a                                            21

<210> SEQ ID NO 87
<211> LENGTH: 18
<212> TYPE: DNA
<213> ORGANISM: Artificial Sequence
<220> FEATURE:
<223> OTHER INFORMATION: synthetic probe

<400> SEQUENCE: 87
tcactcatta gaaattaa                                                18

<210> SEQ ID NO 88
<211> LENGTH: 19
<212> TYPE: DNA
<213> ORGANISM: Artificial Sequence
<220> FEATURE:
<223> OTHER INFORMATION: synthetic probe

<400> SEQUENCE: 88
ctgtaactta gtatcttgc                                               19

<210> SEQ ID NO 89
<211> LENGTH: 18
<212> TYPE: DNA
<213> ORGANISM: Artificial Sequence
<220> FEATURE:
<223> OTHER INFORMATION: synthetic probe

<400> SEQUENCE: 89
acttagtctg atttcctg                                                18

<210> SEQ ID NO 90
<211> LENGTH: 14
<212> TYPE: DNA
<213> ORGANISM: Artificial Sequence
<220> FEATURE:
<223> OTHER INFORMATION: synthetic probe

<400> SEQUENCE: 90
cgaggtgtgg gttg                                                    14

<210> SEQ ID NO 91
<211> LENGTH: 15
<212> TYPE: DNA
<213> ORGANISM: Artificial Sequence
<220> FEATURE:
<223> OTHER INFORMATION: synthetic probe

<400> SEQUENCE: 91
cgaggagtgg gttgt                                                   15

<210> SEQ ID NO 92
<211> LENGTH: 15
<212> TYPE: DNA
<213> ORGANISM: Artificial Sequence
<220> FEATURE:
<223> OTHER INFORMATION: synthetic probe

<400> SEQUENCE: 92
aggcaactgg cacaa                                                   15

<210> SEQ ID NO 93
<211> LENGTH: 14
<212> TYPE: DNA

```
<213> ORGANISM: Artificial Sequence
<220> FEATURE:
<223> OTHER INFORMATION: synthetic probe

<400> SEQUENCE: 93
aggcaaccgg caca                                                    14

<210> SEQ ID NO 94
<211> LENGTH: 20
<212> TYPE: DNA
<213> ORGANISM: Artificial Sequence
<220> FEATURE:
<223> OTHER INFORMATION: synthetic probe

<400> SEQUENCE: 94
acatctctat ccttcactag                                              20

<210> SEQ ID NO 95
<211> LENGTH: 15
<212> TYPE: DNA
<213> ORGANISM: Artificial Sequence
<220> FEATURE:
<223> OTHER INFORMATION: synthetic probe

<400> SEQUENCE: 95
catctccatc cttca                                                   15

<210> SEQ ID NO 96
<211> LENGTH: 20
<212> TYPE: DNA
<213> ORGANISM: Artificial Sequence
<220> FEATURE:
<223> OTHER INFORMATION: synthetic probe

<400> SEQUENCE: 96
tcaaacaaat accacttttc                                              20

<210> SEQ ID NO 97
<211> LENGTH: 16
<212> TYPE: DNA
<213> ORGANISM: Artificial Sequence
<220> FEATURE:
<223> OTHER INFORMATION: synthetic probe

<400> SEQUENCE: 97
aaataccatt tttcta                                                  16

<210> SEQ ID NO 98
<211> LENGTH: 17
<212> TYPE: DNA
<213> ORGANISM: Artificial Sequence
<220> FEATURE:
<223> OTHER INFORMATION: synthetic probe

<400> SEQUENCE: 98
catcatagga cattcta                                                 17

<210> SEQ ID NO 99
<211> LENGTH: 16
<212> TYPE: DNA
<213> ORGANISM: Artificial Sequence
<220> FEATURE:
<223> OTHER INFORMATION: synthetic probe

<400> SEQUENCE: 99
tcatcattgg acattc                                                  16
```

<210> SEQ ID NO 100
<211> LENGTH: 16
<212> TYPE: DNA
<213> ORGANISM: Artificial Sequence
<220> FEATURE:
<223> OTHER INFORMATION: synthetic probe

<400> SEQUENCE: 100
tgccattaaa agaaat                                                   16

<210> SEQ ID NO 101
<211> LENGTH: 14
<212> TYPE: DNA
<213> ORGANISM: Artificial Sequence
<220> FEATURE:
<223> OTHER INFORMATION: synthetic probe

<400> SEQUENCE: 101
tgccattgaa agaa                                                     14

<210> SEQ ID NO 102
<211> LENGTH: 15
<212> TYPE: DNA
<213> ORGANISM: Artificial Sequence
<220> FEATURE:
<223> OTHER INFORMATION: synthetic probe

<400> SEQUENCE: 102
caacacgtga tgagc                                                    15

<210> SEQ ID NO 103
<211> LENGTH: 16
<212> TYPE: DNA
<213> ORGANISM: Artificial Sequence
<220> FEATURE:
<223> OTHER INFORMATION: synthetic probe

<400> SEQUENCE: 103
acaacacatg atgagc                                                   16

<210> SEQ ID NO 104
<211> LENGTH: 19
<212> TYPE: DNA
<213> ORGANISM: Artificial Sequence
<220> FEATURE:
<223> OTHER INFORMATION: synthetic probe

<400> SEQUENCE: 104
aactcaagtt tatgatttg                                                19

<210> SEQ ID NO 105
<211> LENGTH: 20
<212> TYPE: DNA
<213> ORGANISM: Artificial Sequence
<220> FEATURE:
<223> OTHER INFORMATION: synthetic probe

<400> SEQUENCE: 105
actcaagttt aagatttgaa                                               20

<210> SEQ ID NO 106
<211> LENGTH: 18
<212> TYPE: DNA
<213> ORGANISM: Artificial Sequence
<220> FEATURE:

```
<223> OTHER INFORMATION: synthetic probe

<400> SEQUENCE: 106
caaaaccttc atccagtg                                                        18

<210> SEQ ID NO 107
<211> LENGTH: 19
<212> TYPE: DNA
<213> ORGANISM: Artificial Sequence
<220> FEATURE:
<223> OTHER INFORMATION: synthetic probe

<400> SEQUENCE: 107
ccaaaacctt cgtccagtg                                                       19

<210> SEQ ID NO 108
<211> LENGTH: 21
<212> TYPE: DNA
<213> ORGANISM: Artificial Sequence
<220> FEATURE:
<223> OTHER INFORMATION: synthetic probe

<400> SEQUENCE: 108
ctaaataaac taacaattaa c                                                    21

<210> SEQ ID NO 109
<211> LENGTH: 21
<212> TYPE: DNA
<213> ORGANISM: Artificial Sequence
<220> FEATURE:
<223> OTHER INFORMATION: synthetic probe

<400> SEQUENCE: 109
ataaactaca attaacattt g                                                    21

<210> SEQ ID NO 110
<211> LENGTH: 15
<212> TYPE: DNA
<213> ORGANISM: Artificial Sequence
<220> FEATURE:
<223> OTHER INFORMATION: synthetic probe

<400> SEQUENCE: 110
tcccttgcat gtcat                                                           15

<210> SEQ ID NO 111
<211> LENGTH: 16
<212> TYPE: DNA
<213> ORGANISM: Artificial Sequence
<220> FEATURE:
<223> OTHER INFORMATION: synthetic probe

<400> SEQUENCE: 111
cttgcaagtc atgcta                                                          16

<210> SEQ ID NO 112
<211> LENGTH: 17
<212> TYPE: DNA
<213> ORGANISM: Artificial Sequence
<220> FEATURE:
<223> OTHER INFORMATION: synthetic probe

<400> SEQUENCE: 112
tcacgtttgt catgtat                                                         17
```

-continued

```
<210> SEQ ID NO 113
<211> LENGTH: 16
<212> TYPE: DNA
<213> ORGANISM: Artificial Sequence
<220> FEATURE:
<223> OTHER INFORMATION: synthetic probe

<400> SEQUENCE: 113
acgtttgtca agtatg                                                   16

<210> SEQ ID NO 114
<211> LENGTH: 15
<212> TYPE: DNA
<213> ORGANISM: Artificial Sequence
<220> FEATURE:
<223> OTHER INFORMATION: synthetic probe

<400> SEQUENCE: 114
cctcgagctg ttcag                                                    15

<210> SEQ ID NO 115
<211> LENGTH: 14
<212> TYPE: DNA
<213> ORGANISM: Artificial Sequence
<220> FEATURE:
<223> OTHER INFORMATION: synthetic probe

<400> SEQUENCE: 115
ctcgagcggt tcag                                                     14
```